United States Patent [19]
Lambowitz et al.

[11] Patent Number: 6,027,895
[45] Date of Patent: Feb. 22, 2000

[54] METHODS FOR CLEAVING DNA WITH NUCLEOTIDE INTEGRASES

[75] Inventors: Allen M. Lambowitz, Austin, Tex.; Steven Zimmerly, Calgary, Canada; Huatao Gau; Georg Mohr, both of Austin, Tex.; Clifford James Beall, Columbus, Ohio

[73] Assignee: The Ohio State University Research Foundation, Columbus, Ohio

[21] Appl. No.: 09/031,897

[22] Filed: Feb. 27, 1998

Related U.S. Application Data

[60] Continuation-in-part of application No. 08/956,617, Oct. 7, 1997, Pat. No. 5,869,634, which is a division of application No. 08/526,964, Sep. 12, 1995, Pat. No. 5,698,421.
[60] Provisional application No. 60/039,220, Feb. 28, 1997.

[51] Int. Cl.[7] .............. C12Q 1/68; C12P 19/34; A01N 43/04
[52] U.S. Cl. ............ 435/6; 435/91.31; 435/91.1; 435/91.51; 514/44
[58] Field of Search .............. 435/6, 91.31, 91.1, 435/91.51; 514/44

[56] References Cited

U.S. PATENT DOCUMENTS

| | | |
|---|---|---|
| 5,498,531 | 3/1996 | Jarrell . |
| 5,698,421 | 12/1997 | Lambowitz et al. .............. 435/91.1 |

FOREIGN PATENT DOCUMENTS

WO 98/23756  6/1998  WIPO .

OTHER PUBLICATIONS

Lazowska et al.; The EMBO Journal, vol. 13, pp 4963–4972, 1994.

(List continued on next page.)

*Primary Examiner*—Lisa B. Arthur
*Assistant Examiner*—Jehanne Souaya
*Attorney, Agent, or Firm*—Calfee, Halter & Griswold LLP

[57] ABSTRACT

The present invention provides new methods, employing a nucleotide integrase, for cleaving single-stranded RNA substrates, single-stranded DNA substrates, and double-stranded DNA substrates at specific sites and for inserting a nucleic acid molecule into the cleaved substrate. One method uses a nucleotide integrase to cleave one strand of a double-stranded DNA substrate. The method comprises the steps of: providing a nucleotide integrase comprising a group II intron RNA having two hybridizing sequences that are capable of hybridizing with two intron RNA binding sequences on the one strand of the DNA substrate, and a group II-intron encoded protein which binds to a first sequence element of the substrate; and reacting the nucleotide integrase with the double-stranded DNA substrate under conditions that permit the nucleotide integrase to cleave the one strand of the DNA substrate and to insert the group II intron RNA into the cleavage site. The method of cleaving both strands of a double-stranded DNA substrate comprises the steps of: providing a nucleotide integrase comprising a group II intron RNA having two hybridizing sequences that are capable of hybridizing with two intron RNA binding sequences on one strand of the substrate, and a group II-intron encoded protein that is capable of binding to a first sequence element and to a second sequence element in the recognition site of the substrate; and reacting the nucleotide integrase with the double-stranded DNA substrate such that the nucleotide integrase cleaves both strands of the DNA substrate and inserts the group II intron RNA into the cleavage site of the one strand. The method for cleaving a single-stranded nucleic acid substrate comprises the steps of: providing a nucleotide integrase having two hybridizing sequences that are capable of hybridizing with two intron RNA-binding sequences on the single-stranded substrate, and a group II intron encoded protein; and reacting the nucleotide integrase with the single stranded nucleic acid substrate for a time and at a temperature sufficient to allow the nucleotide integrase to cleave the substrate and to attach the group II intron RNA molecule thereto.

27 Claims, 18 Drawing Sheets

OTHER PUBLICATIONS

"A bacterial group II intron encoding reverse transcriptase, maturase, and DNA endonuclease activities: biochemical demonstration of maturase activity and insertion of new genetic information within the intron" by Matsuura, et al., *Genes & Development*, vol. 11, 1997, pp. 2910–2924.

"Group II intron endonucleases use both RNA and protein subunits for recognition of specific sequences in double–stranded DNA" by Guo, et al., *The EMBO Journal*, vol. 16, No. 22, 1997, pp. 6835–6848.

"Efficient integration of an intron RNA into double–stranded DNA by reverse splicing" by Yang, et al., *Nature*, vol. 381, No. 23, May 1996, pp. 332–335.

"Mobility of Yeast Mitochondrial Group II Introns: Engineering a New Site Specifically and Retrohoming via Full Reverse Splicing" by Eskes, et al., *Cell*, vol. 88, Mar. 21, 1997, pp. 865–874.

"Splicing of a Group II Intron Involved in the Conjugative Transfer of pRS01 in Lactococci" by Mills, et al., *Journal of Bacteriology*, vol. 178, No. 12, Jun. 1996, pp. 3531–3538.

"Splicing of a group II intron in a functional transfer gene of *Lactococcus lactis*" by Shearman, et al., *Molecular Microbiology*, vol. 21, 1996, pp. 45–53.

"Targeted DNA cleavage and insertion by group II introns" by Guo, et al., *RNA '97, The second annual meeting of the RNA society*, May 27–Jun. 1, 1997, p. 262.

"A bacterial group II intorn encoding reverse transcriptase, maturase, and DNA endonuclease activities" by Matsuura, et al., *RNA '97, The second annual meeting of the RNA society*, May 27–Jun. 1, 1997, p. 369.

"Novel mechanisms for site–specific DNA cleavage and insertion involving group II intron catalytic RNAs" by Lambowitz, Functional Genomics Conference, Newport, Rhode Island, Nov. 2–5, 1997.

"Group II introns as site–specific retroelements", by Guo, et al., Keystone Symposia on Molecular and Cellular Biology: Transposition and Site–Specific Recombination, Santa Fe, New Mexico, Mar. 1–7, 1997.

"Group II intorn mobility and evolution" by Zimmerly, et al., Keystone Symposia on Molecular and Cellular Biology: Posttranscriptional RNA Processing, Hilton Head, South Carolina, Mach 11–17, 1996.

"Retrotransposition of group II introns" by Zimmerly, et al., Keystone Symposia on Molecular and Cellular Biology: Viral Genome Replication, Tamarron, Colorado, Mar. 1–7, 1996.

"Mitochondrial plasmid and group II intron reverse transcription" by Lambowitz, et al., Keystone Symposia on Molecular and Cellular Biology: Viral Genome Replication, Tamorron, Colorado, Mar. 1–7, 1996.

"Homing of a Group II Intron from *Lactococcus lactis* subsp. *lactis* ML3" by Mills, et al., *Journal of Bacteriology*, Oct. 1997, vol. 179, No. 19, pp. 6107–6111.

Executed Supplemental Information Disclosure Statement of Steven Zimmerly.

Executed Supplemental Information Disclosure Statement of Alan Lambowitz.

"Group I and group II introns" by Saldanha, et al., *The FASEB Journal*, vol. 7, Jan., 1993, pp. 15–24.

"Group II Intron Mobility Occurs to Target DNA–Primed Reverse Transcription" by Zimmerly, et al., *Cell*, vol. 82, Aug. 25, 1995, pp. 545–554.

"An Expanding Universe of Introns" by Belfort, *Science*, vol. 262, Nov. 12, 1993, pp. 1009–1010.

"Integration of Group II Intron b11 into a Foreign RNA by Reversal of the Self–Splicing Reaction in Vitro", by Morl and Schmelzer, *Cell*, vol. 60, Feb. 23, 1990, pp. 629–636.

"A Group II Intron RNA is a Catalytic Component of a DNA Endonuclease Involved in Intron Mobility", by Zimmerly, et al., *Cell*, vol. 83, Nov. 17, 1995, pp. 1–10.

"RNA enzymes (ribozymes) as antiviral therapeutic agents" by Rossi and Sarver, *Tibtech*, vol. 8, Jul., 1990, pp. 179–183.

"Mobile Group II Introns of Yeast Mitochondrial DNA Are Novel Site–Specific Retroelements" by Moran, et al., *Molecular and Cellular Biology*, vol. 15, No. 5, May 1995, pp. 2828–2838.

"Evolutionary relationships among group II intorn–encoded proteins and identification of a conserved domain that may be related to maturase function" by Mohr, et al., *Nucleic Acids Research*, vol. 21, No. 22, 1993, pp. 4991–4997.

"Reverse Trnascriptase Activity Associated with Maturase–Encoding Group II Introns in Yeast Nitochondria" by Kennell, et al., *Cell*, vol. 73, Apr. 9, 1993, pp. 133–146.

"Introns as Mobile Genetic Elements" by Lambowitz, et al., *Annual Reviews Biochem.*, vol. 62, 1993, pp. 587–622.

S. cerevisiae 161 mt coxl E1, aI1, E2, aI2, E3

```
<E1                                                                      60
ATGGTACAAA GATGATTATA TTCAACAAAT GCAAAAGATA TTGCAGTATT ATATTTTATG

120
TTAGCTATTT TTAGTGGTAT GGCAGGAACA GCAATGTCTT TAATCATTAG ATTAGAATTA

E1> aI1    180
GCTGCACCTG GTTCACAATA TTTACATGGT AATTCACAGT TATTTAATGG TGCGCCTCTC

240
AGTGCGTATA TTTCGTTGAT GCGTCTAGCA TTAGTATTAT GAATCATCAA TAGATACTTA

300
AAACATATGA CTAACTCAGT AGGGGCTAAC TTTACGGGGA CAATAGCATG TCATAAAACA

360
CCTATGATTA GTGTAGGTGC AGTTAAGTGT TACATGGTTA GGTTAACGAA CTTCTTACAA

>EBS2<                                                     420
GTCTTTATCA GGATTACAAT TTCCTCTTAT CATTTGGATA TAGTAAAACA AGTTTGATTA

>EBS1<                                                         480
TTTTACGTTG AGGTAATCAG ATTATGATTC ATTGTTTTAG ATAGCACAGG CAGTGTGAAA

540
AAGATGAAGG ACCTAAATAA CACAAAAGGA AATACGAAAA GTGAGGGATC AACTGAAAGA

600
GGAAACTCTT GAGTTGACAG AGGTATAGTA GTACCGAATA CTCAAATAAA AATGAGATTT

660
TTAAATCAAG TTAGATACTA TTCAGTAAAT AATAATTTAA AAATAGGGAA GGATACCAAT

720
ATTGAGTTAT CAAAAGATAC AAGTACTTCG GACTTGTTAG AATTTGAGAA ATTAGTAATA

780
GATAATATAA ATGAGGAAAA TATAAATAAT AATTTATTAA GTATTATAAA AAACGTAGAT

840
ATATTAATAT TAGCATATAA TAGAATTAAG AGTAAACCTG GTAATATAAC TCCAGGTACA
```

MATCH TO FIG.2B

Fig. 2A

MATCH TO FIG.2A

```
                                                                   900
ACATTAGAAA CATTAGATGG TATAAATATA ATATATTTAA ATAAATTATC AAATGAATTA

960
GGAACAGGTA AATTCAAATT TAAACCCATG AGAATAGTTA ATATTCCTAA ACCTAAAGCT

1020
GGTATAAGAC CTTTAAGTGT AGGTAATCCA AGAGATAAAA TTGTACAAGA AGTTATAAGA

1080
ATAATTTTAG ATACAATTTT TGATAAAAAG ATATCAACAC ATTCACATGG TTTTAGAAAG

1140
AATATAAGTT GTCAAACAGC AATTTGAGAA GTTAGAAATA TATTTGGTGG AAGTAATTGA

1200
TTTATTGAAG TAGACTTAAA AAAATGTTTT GATACAATTT CTCATGATTT AATTATTAAA

1260
GAATTAAAAA GATATATTTC AGATAAAGGT TTTATTGATT TAGTATATAA ATTATTAAGA

1320
GCTGGTTATA TTGATGAGAA AGGAACTTAT CATAAACCTA TATTAGGTTT ACCTCAAGGA

1380
TCATTAATTA GTCCTATCTT ATGTAATATT GTAATAACAT TGGTAGATAA TTGATTAGAA

1440
GATTATATTA ATTTATATAA TAAAGGTAAA GTTAAAAAAC AACATCCTAC ATATAAAAAA

1500
TTATCAAGAA TAATTGCAAA AGCTAAAATA TTTTCGACAA GATTAAAATT ACATAAAGAA

1560
AGAGCTAAAG GCCCACTATT TATTTATAAT GATCCTAATT TCAAGAGAAT AAAATACGTT

1620
AGATATGCAG ATGATATTTT AATTGGGGTA TTAGGTTCAA AAAATGATTG TAAAATAATC

1680
AAAAGAGATT TAAACAATTT TTTAAATTCA TTAGGTTTAA CTATAAATGA AGAAAAAACT
```

MATCH TO FIG.2C

Fig. 2B

MATCH TO FIG.2B

```
                                                                  1740
TTAATTACTT GTGCAACTGA ACTACCAGCA AGATTTTTAG GTTATAATAT TTCAATTACA

1800
CCTTTAAAAA GAATACCTAC AGTTACTAAA CTAATTAGAG GTAAACTTAT TAGAAGTAGA

1860
AATACAACTA GACCTATTAT TAATGCACCA ATTAGAGATA TTATCAATAA ATTAGCTACT

1920
AATGGATATT GTAAGCATAA TAAAAATGGT AGAATAGGAG TGCCTACAAG AGTAGGTAGA

1980
TGACTATATG AAGAACCTAG AACAATTATT AATAATTATA AAGCGTTAGG TAGAGGTATC

2040
TTAAATTATT ATAAATTAGC TACTAATTAT AAAAGATTAA GAGAAAGAAT CTATTACGTA

2100
TTATATTATT CATGTGTATT AACTTTAGCT AGTAAATATA GATTAAAAAC ATTAAGTAAA

2160
ACTATTAAAA AATTTGGTTA TAATTTAAAT ATTATTGAAA ATGATAAATT AATTGCCAAT

2220
TTTCCAAGAA ATACTTTTGA TAATATCAAA AAAATTGAAA ATCATGGTAT ATTTATATAT

2280
ATATCAGAAG CTAAAGTAAC TGATCCTTTT GAATATATCG ATTCAATTAA ATATATATTA

2340
CCTACAGCTA AAGCTAATTT TAATAAACCT TGTAGTATTT GTAATTCAAC TATTGATGTA

2400
GAAATACATC ATGTTAAACA ATTACATAGA GGTATATTAA AAGCACTTAA AGATTATATT

2460
CTAGGTAGAA TAATTACCAT AAACAGAAAA CAAATTCCAT TATGTAAACA ATGTCATATT

2520
AAAACACATA AAAATAAATT TAAAAATATA GCACCTGGTA TATAAAATCT ATTATTAATG
```

MATCH TO FIG.2D

Fig. 2C

MATCH TO FIG.2C

```
                                                                    2580
ATACTCAATA TGGAAAGCCG TATGATGGGA AACTATCACG TACGGTTTGG GAAAGGCTCT aI1 > E2                     2640
TTAACACGTG GCAACATAGG TTAATTTGCT ATTACATTTT TAGTAGTTGG TCATGCTGTA

E2 > aI2                                                 2700
TTAATGATTT TCTGTGCGCC GTTTCGCTTA ATTTATCACT GTATTGAAGT GTTAATTGAT

2760
AAACATATCT CTGTTTATTC AATTAATGAA AACTTTACCG TATCATTTTG GTTCTGATTA

2820
TTAGTAGTAA CATACATAGT ATTTAGATAC GTAAACCATA TGGCTTACCC AGTTGGGGCC

2880
AACTCAACGG GGACAATAGC ATGCCATAAA AGCGCTGGAG TAAAACAGCC AGCGCAAGGT

> EBS2 <
AAGAACTGTC CGATGGCTAG GTTAACGAAT TCCTGTAAAG AATGTTTAGG GTTCTCATTA

> EBS1 <             3000
ACTCCTTCCC ACTTGGGGAT TGTGATTCAT GCTTATGTAT TGGAAGAAGA GGTACACGAG

3060
TTAACCAAAA ATGAATCATT AGCTTTAAGT AAAAGTTGAC ATTTGGAGGG CTGTACGAGT

3120
TCAAATGGAA AATTAAGAAA TACGGGATTG TCCGAAAGGG GAAACCCTGS GGATAACGGA

3180
GTCTTCATAG TACCCAAATT TAATTTAAAT AAAGCGAGAT ACTTTAGTAC TTTATCTAAA

3240
TTAAATGCAA GGAAGGAAGA CAGTTTAGCG TATTTAACAA AGATTAATAC TACGGATTTT

3300
TCCGAGTTAA ATAAATTAAT AGAAAATAAT CATAATAAAC TTGAAACCAT TAATACTAGA

3360
ATTTTAAAAT TAATGTCAGA TATTAGAATG TTATTAATTG CTTATAATAA AATTAAAAGT
```

MATCH TO FIG.2E

Fig. 2D

*MATCH TO FIG.2D*

```
                                                                              3420
AAGAAAGGTA ATATATCTAA AGGTTCTAAT AATATTACCT TAGATGGGAT TAATATTTCA
                                                                              3480
TATTTAAATA AATTATCTAA AGATATTAAC ACTAATAYGT TTAAATTTTC TCCGGTTAGA
                                                                              3540
AGAGTTGAAA TTCCTAAAAC ATCTGGAGGA TTTAGACCTT TAAGTGTTGG AAATCCTAGA
                                                                              3600
GAAAAAATTG TACAAGAAAG TATGAGAATA ATATTAGAAA TTATCTATAA TAATAGTTTC
                                                                              3660
TCTTATTATT CTCATGGATT TAGACCTAAC TTATCTTGTT TAACAGCTAT TATTCAATGT
                                                                              3720
AAAAATTATA TGCAATACTG TAATTGATTT ATTAAAGTAG ATTTAAATAA ATGCTTTGAT
                                                                              3780
ACAATTCCAC ATAATATGTT AATTAATGTA TTAAATGAGA GAATCAAAGA TAAAGGTTTC
                                                                              3840
ATAGACTTAT TATATAAATT ATTAAGAGCT GGATATGTTG ATAAAAATAA TAATTATCAT
                                                                              3900
AATACAACTT TAGGAATTCC TCAAGGTAGT GTTGTCAGTC CTATTTTATG TAATATTTTT
                                                                              3960
TTAGATAAAT TAGATAAATA TTTAGAAAAT AAATTTGAGA ATGAATTCAA TACTGGAAAT
                                                                              4020
ATGTCTAATA GAGGTAGAAA TCCAATTTAT AATAGTTTAT CATCTAAAAT TTATAGATGT
                                                                              4080
AAATTATTAT CTGAAAAATT AAAATTGATT AGATTAAGAG ACCATTACCA AAGAAATATG
                                                                              4140
GGATCTGATA AAAGTTTTAA AAGAGCTTAT TTTGTTAGAT ATGCTGATGA TATTATCATT
                                                                              4200
GGTGTAATGG GTTCTCATAA TGATTGTAAA AATATTTTAA ACGATATTAA TAACTTCTTA
```

*MATCH TO FIG.2F*

*Fig. 2E*

MATCH TO FIG. 2E

```
                                                                  4260
AAAGAAAATT TAGGTATGTC AATTAATATA GATAAATCCG TTATTAAACA TTCTAAAGAA
                                                                  4320
GGAGTTAGTT TTTTAGGGTA TGATGTAAAA GTTACACCTT GAGAAAAAAG ACCTTATAGA
                                                                  4380
ATGATTAAAA AAGGTGATAA TTTTATTAGG GTTAGACATC ATACTAGTTT AGTTGTTAAT
                                                                  4440
GCCCCTATTA GAAGTATTGT AATAAAATTA AATAAACATG GCTATTGTTC TCATGGTATT
                                                                  4500
TTAGGAAAAC CCAGAGGGGT TGGAAGATTA ATTCATGAAG AAATGAAAAC CATTTTAATG
                                                                  4560
CATTACTTAG CTGTTGGTAG AGGTATTATA AACTATTATA GATTAGCTAC CAATTTTACC
                                                                  4620
ACATTAAGAG GTAGAATTAC ATACATTTTA TTTTATTCAT GTTGTTTAAC ATTAGCAAGA
                                                                  4680
AAATTTAAAT TAAATACTGT TAAGAAAGTT ATTTTAAAAT TCGGTAAAGT ATTAGTTGAT
                                                                  4740
CCTCATTCAA AAGTTAGTTT TAGTATTGAT GATTTTAAAA TTAGACATAA AATAAATATA
                                                                  4800
ACTGATTCTA ATTATACACC TGATGAAATT TTAGATAGAT ATAAATATAT GTTACCTAGA
                                                                  4860
TCTTTATCAT TATTTAGTGG TATTTGTCAA ATTTGTGGTT CTAAACATGA TTTAGAAGTA
                                                                  4920
CATCACGTAA GAACATTAAA TAATGCTGCC AATAAAATTA AAGATGATTA TTTATTAGGT
                                                                  4980
AGAATGATTA AGATAAATAG AAAACAAATT ACTATCTGTA AACATGTCA TTTTAAAGTT
                                                                  5040
CATCAAGGTA AATATAATGG TCCAGGTTTA TAATAATTAT TATACTCCTT CGGGGTCGCC
```

MATCH TO FIG. 2G

Fig. 2F

```
            10        20        30        40        50        60
AAGCTTAGAGAAAAATAATGCGGTGCTTGGTCATCACCTCATCCAATCATTTTCTCCTGA
TTCGAATCTCTTTTTATTACGCCACGAACCAGTAGTGGAGTAGGTTAGTAAAAGAGGACT 70        80        90       100       110       120
TGACAATCTAACTCCTGAACAAATTCATGAAATAGGTCGTCAAACCATATTAGAATTTAC   LtrB. E1
ACTGTTAGATTGAGGACTTGTTTAAGTACTTTATCCAGCAGTTTGGTATAATCTTAAATG 130       140       150       160       170       180
AGGTGGCGAATATGAATTTGTGATTGCAACCCACGTCGATCGTGAACACATCCATAACGT   LtrBI
TCCACCGCTTATACTTAAACACTAACGTTGGGTGCAGCTAGCACTTGTGTAGGTATTGCA 190       200       210       220       230       240
GCGCCCAGATAGGGTGTTAAGTCAAGTAGTTTAAGGTACTACTCTGTAAGATAACACAGA
CGCGGGTCTATCCCACAATTCAGTTCATCAAATTCCATGATGAGACATTCTATTGTGTCT 250       260       270       280       290       300
AAACAGCCAACCTAACCGAAAAGCGAAAGCTGATACGGGAACAGAGCACGGTTGGAAAGC
TTTGTCGGTTGGATTGGCTTTTCGCTTTCGACTATGCCCTTGTCTCGTGCCAACCTTTCG 310       320       330       340       350       360
GATGAGTTACCTAAAGACAATCGGGTACGACTGAGTCGCAATGTTAATCAGATATAAGGT
CTACTCAATGGATTTCTGTTAGCCCATGCTGACTCAGCGTTACAATTAGTCTATATTCCA 370       380       390       400  EBS2  410       420
ATAAGTTGTGTTTACTGAACGCAAGTTTCTAATTTCGGTTATGTGTCGATAGAGGAAAGT
TATTCAACACAAATGACTTGCGTTCAAAGATTAAAGCCAATACACAGCTATCTCCTTTCA

┌EBS1
           430       440       450       460  \    470       480
GTCTGAAACCTCTAGTACAAAGAAAGGTAAGTTATGGTTGTGGACTTATCTGTTATCACC
CAGACTTTGGAGATCATGTTTCTTTCCATTCAATACCAACACCTGAATAGACAATAGTGG 490       500       510       520       530       540
ACATTTGTACAATCTGTAGGAGAACCTATGGGAACGAAACGAAAGCGATGCCGAGAATCT
TGTAAACATGTTAGACATCCTCTTGGATACCCTTGCTTTGCTTTCGCTACGGCTCTTAGA 550       560       570       580       590       600
GAATTTACCAAGACTTAACACTAACTGGGGATACCCTAAACAAGAATGCCTAATAGAAAG
CTTAAATGGTTCTGAATTGTGATTGACCCCTATGGGATTTGTTCTTACGGATTATCTTTC
```

MATCH TO FIG. 10B

*Fig. 10A*

MATCH TO FIG.10A

```
       610       620       630       640       650       660
GAGGAAAAAGGCTATAGCACTAGAGCTTGAAAATCTTGCAAGGGTACGGAGTACTCGTAG
CTCCTTTTTCCGATATCGTGATCTCGAACTTTTAGAACGTTCCCATGCCTCATGAGCATC 670       680       690       700       710       720
TAGTCTGAGAAGGGTAACGCCCTTTACATGGCAAAGGGGTACAGTTATTGTGTACTAAAA
ATCAGACTCTTCCCATTGCGGGAAATGTACCGTTTCCCCATGTCAATAACACATGATTTT
                                  ──→LtrA ORF
       730       740       750  |   760       770       780
TTAAAAATTGATTAGGGAGGAAAACCTCAAAATGAAACCAACAATGGCAATTTTAGAAAG
AATTTTTAACTAATCCCTCCTTTTGGAGTTTTACTTTGGTTGTTACCGTTAAAATCTTTC 790       800       810       820       830       840
AATCAGTAAAAATTCACAAGAAAATATAGACGAAGTTTTTACAAGACTTTATCGTTATCT
TTAGTCATTTTTAAGTGTTCTTTTATATCTGCTTCAAAAATGTTCTGAAATAGCAATAGA 850       860       870       880       890       900
TTTACGTCCAGATATTTATTACGTGGCGTATCAAAATTTATATTCCAATAAAGGAGCTTC
AAATGCAGGTCTATAAATAATGCACCGCATAGTTTTAAATATAAGGTTATTTCCTCGAAG 910       920       930       940       950       960
CACAAAAGGAATATTAGATGATACAGCGGATGGCTTTAGTGAAGAAAAAATAAAAAAGAT
GTGTTTTCCTTATAATCTACTATGTCGCCTACCGAAATCACTTCTTTTTTATTTTTTCTA 970       980       990      1000      1010      1020
TATTCAATCTTTAAAAGACGGAACTTACTATCCTCAACCTGTACGAAGAATGTATATTGC
ATAAGTTAGAAATTTTCTGCCTTGAATGATAGGAGTTGGACATGCTTCTTACATATAACG 1030      1040      1050      1060      1070      1080
AAAAAAGAATTCTAAAAAGATGAGACCTTTAGGAATTCCAACTTTCACAGATAAATTGAT
TTTTTTCTTAAGATTTTTCTACTCTGGAAATCCTTAAGGTTGAAAGTGTCTATTTAACTA 1090      1100      1110      1120      1130      1140
CCAAGAAGCTGTGAGAATAATTCTTGAATCTATCTATGAACCGGTATTCGAAGATGTGTC
GGTTCTTCGACACTCTTATTAAGAACTTAGATAGATACTTGGCCATAAGCTTCTACACAG 1150      1160      1170      1180      1190      1200
TCACGGTTTTAGACCTCAACGAAGCTGTCACACAGCTTTGAAAACAATCAAAAGAGAGTT
AGTGCCAAAATCTGGAGTGGCTTCGACAGTGTGTCGAAACTTTTGTTAGTTTTCTCTCAA
```

MATCH TO FIG.10C

Fig. 10B

MATCH TO FIG.10B 1210  1220  1230  1240  1250  1260
TGGCGGCGCAAGATGGTTTGTGGAGGGAGATATAAAAGGCTGCTTCGATAATATAGACCA
ACCGCCGCGTTCTACCAAACACCTCCCTCTATATTTTCCGACGAAGCTATTATATCTGGT 1270  1280  1290  1300  1310  1320
CGTTACACTCATTGGACTCATCAATCTTAAAATCAAAGATATGAAAATGAGCCAATTGAT
GCAATGTGAGTAACCTGAGTAGTTAGAATTTTAGTTTCTATACTTTTACTCGGTTAACTA 1330  1340  1350  1360  1370  1380
TTATAAATTTCTAAAAGCAGGTTATCTGGAAAACTGGCAGTATCACAAAACTTACAGCGG
AATATTTAAAGATTTTCGTCCAATAGACCTTTTGACCGTCATAGTGTTTTGAATGTCGCC 1390  1400  1410  1420  1430  1440
AACACCTCAAGGTGGAATTCTATCTCCTCTTTTGGCCAACATCTATCTTCATGAATTGGA
TTGTGGAGTTCCACCTTAAGATAGAGGAGAAAACCGGTTGTAGATAGAAGTACTTAACCT 1450  1460  1470  1480  1490  1500
TAAGTTTGTTTTACAACTCAAAATGAAGTTTGACCGAGAAAGTCCAGAAAGAATAACACC
ATTCAAACAAAATGTTGAGTTTTACTTCAAACTGGCTCTTTCAGGTCTTTCTTATTGTGG 1510  1520  1530  1540  1550  1560
TGAATATCGGGAACTTCACAATGAGATAAAAAGAATTTCTCACCGTCTCAAGAAGTTGGA
ACTTATAGCCCTTGAAGTGTTACTCTATTTTTCTTAAAGAGTGGCAGAGTTCTTCAACCT 1570  1580  1590  1600  1610  1620
GGGTGAAGAAAAAGCTAAAGTTCTTTTAGAATATCAAGAAAAACGTAAAAGATTACCCAC
CCCACTTCTTTTTCGATTTCAAGAAAATCTTATAGTTCTTTTTGCATTTTCTAATGGGTG 1630  1640  1650  1660  1670  1680
ACTCCCCTGTACCTCACAGACAAATAAAGTATTGAAATACGTCCGGTATGCGGACGACTT
TGAGGGGACATGGAGTGTCTGTTTATTTCATAACTTTATGCAGGCCATACGCCTGCTGAA 1690  1700  1710  1720  1730  1740
CATTATCTCTGTTAAAGGAAGCAAAGAGGACTGTCAATGGATAAAAGAACAATTAAAACT
GTAATAGAGACAATTTCCTTCGTTTCTCCTGACAGTTACCTATTTTCTTGTTAATTTTGA 1750  1760  1770  1780  1790  1800
TTTTATTCATAACAAGCTAAAAATGGAATTGAGTGAAGAAAAAACACTCATCACACATAG
AAAATAAGTATTGTTCGATTTTTACCTTAACTCACTTCTTTTTTGTGAGTAGTGTGTATC

MATCH TO FIG.10D

Fig. 10C

MATCH TO FIG. 10C

```
       1810      1820      1830      1840      1850      1860
CAGTCAACCCGCTCGTTTTCTGGGATATGATATACGAGTAAGGAGAAGTGGAACGATAAA
GTCAGTTGGGCGAGCAAAAGACCCTATACTATATGCTCATTCCTCTTCACCTTGCTATTT 1870      1880      1890      1900      1910      1920
ACGATCTGGTAAAGTCAAAAAGAGAACACTCAATGGGAGTGTAGAACTCCTTATTCCTCT
TGCTAGACCATTTCAGTTTTTCTCTTGTGAGTTACCCTCACATCTTGAGGAATAAGGAGA 1930      1940      1950      1960      1970      1980
TCAAGACAAAATTCGTCAATTTATTTTTGACAAGAAAATAGCTATCCAAAAGAAAGATAG
AGTTCTGTTTTAAGCAGTTAAATAAAAACTGTTCTTTTATCGATAGGTTTTCTTTCTATC 1990      2000      2010      2020      2030      2040
CTCATGGTTTCCAGTTCACAGGAAATATCTTATTCGTTCAACAGACTTAGAAATCATCAC
GAGTACCAAAGGTCAAGTGTCCTTTATAGAATAAGCAAGTTGTCTGAATCTTTAGTAGTG 2050      2060      2070      2080      2090      2100
AATTTATAATTCTGAATTAAGAGGGATTTGTAATTACTACGGTCTAGCAAGTAATTTTAA
TTAAATATTAAGACTTAATTCTCCCTAAACATTAATGATGCCAGATCGTTCATTAAAATT 2110      2120      2130      2140      2150      2160
CCAGCTCAATTATTTTGCTTATCTTATGGAATACAGCTGTCTAAAAACGATAGCCTCCAA
GGTCGAGTTAATAAAACGAATAGAATACCTTATGTCGACAGATTTTGCTATCGGAGGTT 2170      2180      2190      2200      2210      2220
ACATAAGGGAACACTTTCAAAAACCATTTCCATGTTTAAAGATGGAAGTGGTTCGTGGGG
TGTATTCCCTTGTGAAAGTTTTTGGTAAAGGTACAAATTTCTACCTTCACCAAGCACCCC 2230      2240      2250      2260      2270      2280
CATCCCGTATGAGATAAAGCAAGGTAAGCAGCGCCGTTATTTGCAAATTTTAGTGAATG
GTAGGGCATACTCTATTTCGTTCCATTCGTCGCGGCAATAAAACGTTTAAAATCACTTAC 2290      2300      2310      2320      2330      2340
TAAATCCCCTTATCAATTTACGGATGAGATAAGTCAAGCTCCTGTATTGTATGGCTATGC
ATTTAGGGGAATAGTTAAATGCCTACTCTATTCAGTTCGAGGACATAACATACCGATACG 2350      2360      2370      2380      2390      2400
CCGGAATACTCTTGAAAACAGGTTAAAAGCTAAATGTTGTGAATTATGTGGAACATCTGA
GGCCTTATGAGAACTTTTGTCCAATTTTCGATTTACAACACTTAATACACCTTGTAGACT
```

MATCH TO FIG. 10E

*Fig. 10D*

MATCH TO FIG. 10D

```
       2410      2420      2430      2440      2450      2460
TGAAAATACTTCCTATGAAATTCACCATGTCAATAAGGTCAAAAATCTTAAAGGCAAAGA
ACTTTTATGAAGGATACTTTAAGTGGTACAGTTATTCCAGTTTTTAGAATTTCCGTTTCT 2470      2480      2490      2500      2510      2520
AAAATGGGAAATGGCAATGATAGCGAAACAACGTAAAACTCTTGTTGTATGCTTTCATTG
TTTTACCCTTTACCGTTACTATCGCTTTGTTGCATTTTGAGAACAACATACGAAAGTAAC
                                    ┌──→LtrA ORF
       2530      2540      2550     │ 2560      2570      2580
TCATCGTCACGTGATTCATAAACACAAGTGAATTTTTACQAACGAACAATAACAGAGCCG
AGTAGCAGTGCACTAAGTATTTGTGTTCACTTAAAAATGCTTGCTTGTTATTGTCTCGGC 2590      2600      2610      2620      2630      2640
TATACTCCGAGAGGGGTACGTACGGTTCCCGAAGAGGGTGGTGCAAACCAGTCACAGTAA      LtrBI
ATATGAGGCTCTCCCCATGCATGCCAAGGGCTTCTCCCACCACGTTTGGTCAGTGTCATT 2650      2660      2670│  2680      2690      2700
TGTGAACAAGGCGGTACCTCCCTACTTCACCATATCATTTTTAATTCTACGAATCTTTAT      LtrB.E2
ACACTTGTTCCGCCATGGAGGGATGAAGTGGTATAGTAAAAATTAAGATGCTTAGAAATA 2710      2720      2730      2740      2750      2760
ACTGGCAAACAATTTGACTGGAAAGTCATTCCTAAAGAGAAAACAAAAAGCGGCAAAGCT
TGACCGTTTGTTAAACTGACCTTTCAGTAAGGATTTCTCTTTTGTTTTTCGCCGTTTCGA
```

METHODS FOR CLEAVING DNA WITH NUCLEOTIDE INTEGRASES

This application claims benefit of Provisional application Ser. No. 60/039,220 Feb. 28, 1997.

CROSS-REFERENCE TO RELATED APPLICATIONS

This application is a continuation-in-part of the commonly assigned, U.S. patent application Ser. No. 08/956,617, filed Oct. 7, 1997, which issued on Feb. 19, 1999, as U.S. Pat. No. 5,869,634, and which is a divisional of U.S. application Ser. No. 08/526,964, filed on Sep. 12, 1995, which issued on Dec. 16, 1997, as U.S. Pat. No. 5,698,421.

The present invention was made with support from National Institutes of Health Grant NO. GM37949. The United States Government has certain rights in the invention.

BACKGROUND

In recent years, a number of methods have been developed for manipulating DNA. Some of these methods employ biomolecules to cut or cleave DNA, which in some instances renders the substrate DNA nonfunctional. Other methods employ biomolecules to facilitate insertion of new pieces of nucleic acid into the cleavage site of the DNA substrate. The insertion of new segments of nucleic acid into the cleavage sites of the DNA substrate changes the characteristics of the RNA or protein molecules encoded by the substrate DNA molecules. Accordingly, the biomolecules which catalyze the cleavage of DNA substrates or the insertion of new nucleic acid molecules into the DNA substrates are useful tools for genetic engineering, for analytical studies and for diagnostic studies. One such molecule used for cleaving DNA substrates is the restriction endonuclease.

Restriction endonucleases are enzymatic proteins that cleave double-stranded DNA. Such endonucleases recognize specific nucleotide sequences in double-stranded DNA, and cleave both strands within or near the specific recognition site. Such specificity renders the restriction endonucleases important tools in the controlled fragmentation of double-stranded DNA. Restriction endonucleases are also useful analytical tools for determining whether certain sequences are present in substrate DNA and in genomic sequencing studies.

However, restriction endonucleases only cleave DNA substrates; they do not insert new nucleic acid molecules into the cleaved DNA substrate. Accordingly, another biomolecule is needed to insert new pieces of DNA or RNA into the double-stranded DNA.

Ribozymes are catalytic RNA molecules that cleave RNA and, in certain circumstances, that insert new pieces of RNA into the cleavage site of the RNA substrate. Unfortunately, ribozymes have not been particularly useful for cleaving single-stranded DNA substrates or double-stranded DNA substrates. Ribozymes cut single-stranded DNA only under extreme conditions of elevated temperatures and high concentrations of magnesium. Ribozymes can be used to cleave double-stranded DNA only after the DNA is denatured and separated into two pieces of single-stranded DNA. Moreover, ribozymes have limited use in systems containing ribonucleases.

Accordingly, it is desirable to have new methods that employ a new tool that is capable of cleaving double-stranded DNA molecules, single-stranded DNA molecules, and single-stranded RNA molecules at specific sites. Methods which employ a new biomolecule capable of cleaving RNA molecules, single-stranded DNA molecules and double-stranded DNA molecules at specific sites and simultaneously inserting a new nucleic acid molecule into the cleavage site are especially desirable.

SUMMARY OF THE INVENTION

The present invention provides new methods, employing a nucleotide integrase, for cleaving single-stranded RNA substrates, single-stranded DNA substrates, and double-stranded DNA substrates at specific sites and for inserting nucleic acid molecules into the cleaved substrate. The nucleotide integrase is a ribonucleoprotein particle comprising a group II intron RNA and a group II intron-encoded protein, which is bound to the group II intron RNA.

One method uses a nucleotide integrase to cleave one strand, hereinafter referred to as the "top strand" of a double stranded DNA substrate. As denoted herein, nucleotides that are located upstream of the cleavage site on the top strand have a (−) position relative to the cleavage site, and nucleotides that are located downstream of the cleavage site have a (+) position relative to the cleavage site. Thus, the cleavage site is located between nucleotides −1 and +1 on the top strand of the double-stranded DNA substrate. The top strand of the substrate comprises a first intron RNA binding sequence, hereinafter referred to as the "IBS1" sequence and a second intron RNA binding sequence, hereinafter referred to as the "IBS2" sequence. The IBS1 sequence and IBS2 sequence lie in a region which extends from about position −1 to about position −14 relative to the cleavage site. The first 10 to 12 pairs of nucleotides that lie upstream of IBS2 and IBS1, i.e from about position −12 relative to the cleavage site to about position −24 relative to the cleavage site are hereinafter collectively referred to as "the first sequence element". The first 10 to 12 pairs of nucleotide that lie downstream of the cleavage site are hereinafter collectively referred to as "the second sequence element".

The method comprises the steps of: providing a nucleotide integrase comprising a group II intron RNA having two hybridizing sequences, "EBS1" and "EBS2", that are capable of hybridizing with the IBS1 sequence and IBS2 sequence, respectively, on the top strand of the DNA substrate, and a group II-intron encoded protein which binds to at least one nucleotide in the first sequence element of the substrate; and reacting the nucleotide integrase with the double-stranded DNA substrate under conditions that permit the nucleotide integrase to cleave the top strand of the DNA substrate and to insert the group II intron RNA into the cleavage site. Preferably, the nucleotide immediately preceding the first nucleotide of the EBS1 sequence on the group II intron RNA, hereinafter referred to as the δ nucleotide is complementary to the nucleotide at +1 on the top strand of the substrate, hereinafter referred to as the 67' nucleotide. The EBS1 sequence of the group II intron RNA comprises from about 5 to 7 nucleotides and has substantial complementarity with the nucleotides at positions −1 to about −5 or about −7 on the top strand of the DNA substrate. The EBS2 sequence comprises from about 4 to 7 nucleotides and has substantial complementarity with the nucleotides at positions from about −6 to about −14 on the top strand of the DNA substrate.

The present invention also provides a method which employs a nucleotide integrase to cleave both strands of a double-stranded DNA substrate. The method comprises the steps of: providing a nucleotide integrase comprising a group II intron RNA having two hybridizing sequences, EBS1 and EBS2, that are capable of hybridizing with two intron RNA binding sequences, IBS1 and IBS2, on the top strand of the substrate, and a group II-intron encoded protein that is capable of binding to at least one nucleotide in the first sequence element and to at least one nucleotide in a second sequence element in the recognition site of the substrate; and reacting the nucleotide integrase with the double-stranded DNA substrate such that the nucleotide integrase cleaves both strands of the DNA substrate and inserts the group II intron RNA into the cleavage site of the top strand. Preferably, the δ nucleotide of the group II intron RNA is complementary to the 67' nucleotide on the top strand of the substrate.

Another method provided by the present invention employs a nucleotide integrase for cleaving a single-stranded nucleic acid substrate and for inserting the group II intron RNA of the nucleotide integrase into the cleavage site. The method comprises the steps of: providing a nucleotide integrase having two hybridizing sequences, EBS1 and EBS2, that are capable of hybridizing with two intron RNA-binding sequences, IBS1 and IBS2, on the single-stranded substrate, and a group II intron encoded protein; and reacting the nucleotide integrase with the single stranded nucleic acid substrate for a time and at a temperature sufficient to allow the nucleotide integrase to cleave the substrate and to attach the group II intron RNA molecule thereto. The EBS1 sequence of the group II intron RNA comprises from about 5 to 7 nucleotides that have substantial complementarity with the nucleotides at positions −1 to about −5 or about −7 relative to the putative cleavage site. The EBS2 sequence comprises from about 4 to 7 nucleotides that have substantial complementarity with the nucleotides at positions from about −6 to about −14 relative to the putative cleavage site. Preferably, the 6 nucleotide of the group II intron RNA is complementary to the δ nucleotide on the top strand of the substrate.

The present invention also relates to a method of determining whether a nucleic acid comprises a particular recognition site. The method comprises the steps of providing a nucleotide integrase capable of cleaving a nucleic acid comprising a particular recognition site; reacting the nucleotide integrase with the nucleic acid; and assaying for cleavage of the nucleic acid, wherein cleavage of the nucleic acid indicates that the nucleic acid comprises the recognition site.

BRIEF DESCRIPTION OF THE DRAWING

FIG. 2 is a diagram depicting the nucleotide sequence and the of the aI2 intron RNA, SEQ.ID.NO. 1 and the nucleotide sequence of the group II intron RNA of the first intron of the *S. cerevisiae* mitochondrial COX1 gene, hereinafter referred to as the "aI1 intron" RNA, SEQ.ID.NO.2. Markings above the sequence identify the position of the EBS1 sequence and the EBS2 sequence of the wild-type aI1 intron RNA and the wild-type aI2 intron RNA.

FIG. 10 shows the Ll.ltrB intron DNA sequence and portions of the nucleotide sequence of the flanking exons ltrBE1 and ltrBE2, SEQ.ID.NO.5, the nucleotide sequence of the open reading frame, of the Ll.ltrB intron SEQ. ID. NO. 6 and the amino acid sequence of the ltrA protein, SEQ.ID.NO. 7.

DETAILED DESCRIPTION OF THE INVENTION

The present invention provides new methods that employ a nucleotide integrase for manipulating DNA and RNA substrates.

One method uses a nucleotide integrase to cleave one strand, hereinafter referred to as the top strand, of a double-stranded DNA at a specific site and to concomitantly attach a nucleic acid molecule, which comprises an RNA molecule, to the cleaved strand at the cleavage site. The DNA substrate has a recognition site which comprises a first intron RNA binding sequence (IBS1) that is located on the top strand of the substrate and upstream of the cleavage site and a second intron RNA binding sequence (IBS2) that is located on the top strand of the DNA substrate and upstream of the IBS1 sequence. The recognition site also comprises a first sequence element that is located upstream of the IBS2 sequence. The first sequence element comprises from about 10 to 12 pairs of nucleotides.

The method of cleaving the top strand of a double-stranded DNA substrate comprises the steps of: providing a nucleotide integrase comprising a group II intron RNA having an EBS1 sequence and an EBS2 sequence that are capable of hybridizing with the IBS1 sequence and the IBS2, respectively on the top strand of the DNA substrate, and a group II-intron encoded protein capable of binding to at least one nucleotide in the first sequence element; and reacting the nucleotide integrase with the double-stranded DNA substrate for a time and at a temperature sufficient to permit the nucleotide integrase to cleave the top strand of the DNA substrate and to insert the group II intron RNA into the cleavage site. Preferably, the group II intron-encoded protein binds to a plurality of nucleotides in the first sequence element.

The nucleotide integrase employed in this method comprises a group II intron-encoded protein bound to an excised group II intron RNA. The EBS1 sequence and EBS2 sequence of the group II intron RNA have at least 80%, preferably 90%, more preferably full complementarity with the IBS1 sequence and IBS2 sequence, respectively, that are on the top strand of the substrate. The group II intron-encoded protein comprises an RT domain, an X domain, and the non-conserved portion of the Zn domain.

Figure 1:
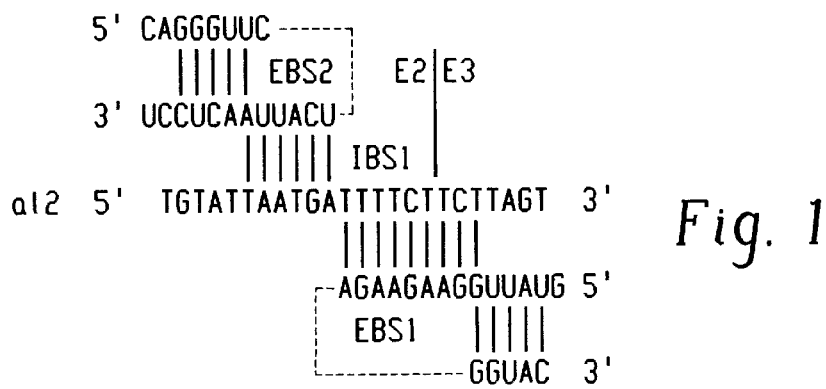
FIG. 1 is a diagram of showing the interaction between the EBS sequences of a group II intron RNA of the second intron of the *S. cerevisiae* mitochondrial COX1 gene, hereinafter referred to as the "aI2 intron" RNA and the IBS sequences of a DNA substrate. The cleavage site in the substrate is represented by an arrow.

EBS1 is located in domain I of the group II intron RNA and comprises from about 5 to 7 nucleotides that are capable of hybridizing to the nucleotides of the IBS1 sequence of the substrate. EBS2 is located in domain I of the group II intron RNA upstream of EBS1 and comprises from about 4 to 7 nucleotides that are capable of hybridizing to the nucleotides of IBS2 sequence of the substrate. If the nucleotides of the EBS1 and EBS2 sequences of the group II intron RNA are not at least 80% complementary to the nucleotides of the IBS1 or IBS2 sequences, respectively, then the group II intron RNA is modified to increase the complementarity between the EBS and IBS sequences. As shown in FIG. 1 the IBS1 sequence of the substrate is upstream of the cleavage site and the IBS2 sequence of the substrate is upstream of the IBS1 sequence.

In order to cleave the substrate efficiently, it is preferred that the nucleotide, δ, which immediately precedes the first nucleotide of EBS1 of the group II intron RNA, be complementary to the nucleotide at +1 in the top strand. Thus, if the δ nucleotide is not complementary to the nucleotide at +1 on the top strand of the substrate, the group II intron RNA is modified to contain a delta nucleotide which is complementary to the nucleotide at +1 on the top strand of the substrate. The nucleotide integrase is then reacted with the substrate. Suitable nucleotide integrases for use in this method include, for example the aI2 nucleotide integrase, the aI1 nucleotide integrase, and the ltrA nucleotide integrase.

The aI2 integrase comprises a wild-type or modified group II intron RNA of the second intron of the *S. cerevisiae* mitochondrial COX1 gene, hereinafter referred to as the "aI2 intron" RNA, bound to a wild-type or modified aI2 intron encoded-protein. The sequence of the wild-type aI2 intron RNA is depicted in FIG. 1 and SEQ. ID. NO. 1. The sequence of the protein encoded by the wild-type aI2 intron RNA is set forth in SEQ. ID. NO. 3. EBS1 of the aI2 intron RNA comprises 6 nucleotides and is located at position 2985–2990 of the sequence set forth in SEQ. ID. NO. 1. EBS1 of the wild-type aI2 intron RNA has the sequence 5'-AGAAGA. The EBS2 sequence of the aI2 intron RNA comprises 6 nucleotides and is located at positions 2935–2940. The EBS2 sequence of the wild-type aI2 intron RNA has the sequence 5'-UCAUUA.

aI2 nucleotide integrases are used to cleave substrates that have on the top strand thereof a T at positions −15 and −13 relative to the putative cleavage site, a C at position −18 relative to the putative cleavage site, and a G at position −16 or position −19 relative to the putative cleavage site. Thus, to use the aI2 nucleotide integrase, one first examines the sequence of the top strand of the substrate to locate a target sequence 5'GCXXTXT or a target sequence 5'XCXGTXT, wherein X represents A, C, G, or T and wherein A represents a nucleotide having an adenine base, G represents a nucleotide having a guanine base, C represents a nucleotide have a cytosine base, and T represents a nucleotide have a thymine base. Then, if the EBS2 sequence of the aI2 intron RNA does not have substantial complementarity to the IBS2 sequence, i.e., the sequence of 6 nucleotides that lie immediately downstream from one of these target sequences, and/or if EBS1 sequence of the aI2 intron RNA does not have substantial complementarity to the IBS1 sequence, i.e., the sequence of six nucleotides that lie immediately downstream of the IBS2 sequence, then EBS1 and EBS2 are modified to have substantial complementarity, as hereinafter explained. The efficiency of cleavage by the aI2 nucleotide integrase is increased if the top strand of the substrate has an A at −21, a G at −19, a C at −18, a G at −16, a T at −15, and a T at −13.

The aI1 nucleotide integrase comprises an excised, wild-type or modified excised group II intron RNA of the first intron of the *S. cerevisiae* mitochondrial COX1 gene, hereinafter referred to as the "aI1 intron" RNA, and a wild-type or modified aI1 intron-encoded protein. The sequence of the aI1 intron RNA is shown in FIG. 2 and SEQ. ID. NO. 2. The sequence of the protein encoded by the aI1 intron RNA is set forth in SEQ. ID. NO. 4. The EBS1 sequence of the aI1 intron RNA comprises 6 nucleotides and is located at position 426–431. EBS1 of the wild-type aI1 intron RNA has the sequence 5'-CGUUGA. The EBS2 sequence of the aI1 intron RNA comprises 6 nucleotides and is located at positions 376–381. EBS2 of the wild-type aI1 intron RNA and has the sequence 5'-ACAAUU.

aI1 nucleotide integrases are used to cleave the top strand of double stranded DNA substrates that have on the top strand thereof a C at position −13 relative to the putative cleavage site. Preferably, the top strand of the substrate has a C at −13, a G at −22, a G at −21 an A at −19 and an A at −18 relative to the putative cleavage site. If the EBS2 sequence of the aI1 intron RNA does not have substantial complementarity to the IBS2 sequence, i.e., the sequence of 6 nucleotides that lie immediately downstream from the C nucleotide at −13, and/or if EBS1 sequence of the aI1 intron RNA does not have substantial complementarity to the IBS1 sequence, i.e., the sequence of six nucleotides that lie immediately downstream of the IBS2 sequence and immediately upstream of the cleavage site, then the EBS1 sequence and the EBS2 sequence of the group II intron RNA are modified to have substantial complementarity, as hereinafter explained.

The ltrA nucleotide integrase comprises an excised, wild-type or modified excised group Ll.ltrB group II intron RNA of the Lactococcus lactis ltrB gene, hereinafter referred to as the "Ll.ltrB intron" RNA, and a wild-type or modified Ll.ltrB intron-encoded protein, hereinafter referred to as the ltrA protein. The sequence of the Ll.ltrB intron RNA is shown in FIG. 10 and SEQ. ID. NO. 5. The sequence of the ltrA protein is set forth in SEQ. ID. NO.7. The EBS1 sequence of the Ll.ltrB intron RNA comprises 7 nucleotides and is located at positions 457 to 463. The EBS1 sequence of the wild-type Ll.ltrB intron RNA has the sequence 5'-GUUGUGG. The EBS2 of the Ll.ltrB intron RNA comprises 6 nucleotides and is located at positions 401 to and including 406. The EBS2 sequence of the wild-type Ll.ltrB intron RNA has the Sequence 5'AUGUGU. The ltrA nucleotide integrase is used to cleave the top strand of a double-stranded DNA substrate when the top strand has a G at −21 and an A at −20 relative to the cleavage site. The ltrA nucleotide integrase cuts the top strand more efficiently when there is a G at −21,an A at −20, a T at −19,a G at −17,and a G at −15.

Another method uses a nucleotide integrase for cleaving both strands of double-stranded DNA and for attaching the group II intron RNA molecule into the cleavage site of the top strand of the DNA substrate. The nucleotide integrase comprises a group II intron-encoded protein bound to an excised group II intron RNA, wherein the group II intron RNA has an EBS1 sequence and an EBS2 sequence that have substantial complementarity to the IBS1 sequence and IBS2 sequence, respectively, on the top strand of the substrate. The EBS1 sequence comprises from about 5 to 7 nucleotides. The EBS2 sequence comprises from about 4 to 7 nucleotides. If the nucleotides of EBS1 and EBS2 of the group II intron RNA are not at least 80% complementary to the nucleotides of IBS1 and IBS2, the non-complementary nucleotides are modified, preferably, by recombinant techniques. Preferably, the δ nucleotide of the group II intron RNA is complementary to the nucleotide at +1 in the top strand. If the δ nucleotide is not complementary to the nucleotide at +1, preferably the δ nucleotide is modified to be complementary. The group II intron-encoded protein comprises an RT domain, an X domain, and the conserved and non-conserved regions of a Zn domain. To insert a cDNA into the cleavage site on the bottom strand of the substrate, the group II intron-encoded protein also comprises a reverse transcriptase domain.

The method of cleaving both strands of a double-stranded DNA sequence having a recognition site comprises the steps of: providing a nucleotide integrase comprising a group II intron RNA having two sequences, EBS1 and EBS2, that are capable of hybridizing with two intron RNA-binding sequences, IBS1 and IBS2, on the top strand of the DNA substrate, and a group II-intron encoded protein that binds to a first sequence element and to a second sequence element in the recognition site of the substrate; and reacting the nucleotide integrase with the double-stranded DNA substrate for a time and at a temperature sufficient to permit the nucleotide integrase to cleave both strands of the DNA substrate and to insert the group II intron RNA into the cleavage site of the top strand. The first sequence element of the recognition site is upstream of the putative cleavage site, the IBS1 sequence and the IBS2 sequence. The first sequence element comprises from about 10 to about 12 pairs of nucleotides. The second sequence element comprises from about 10 to about 12 nucleotides and lies downstream of the cleavage site, i.e., from position +1 to about position +10, +11, or +12.

Nucleotide integrases that may be employed to cleave both strands of a DNA substrate include, but are not limited to an aI2 nucleotide integrase, an aI1 nucleotide integrase, and an ltrA nucleotide integrase. The preferred recognition site for the aI2 nucleotide integrase comprises on the top strand thereof a C at −18, a T at −15, a T at −13, a G at −16 or −19, a T at +1, a T at +4, and a G at +6 relative to the cleavage site. To use the aI2 nucleotide integrase to cleave both strands of the DNA substrate, one first examines the substrate sequence to determine if one strand thereof contains this set of nucleotides. Then, if the EBS2 sequence of the aI2 intron RNA does not have substantial complementarity to the IBS2 sequence of the substrate, i.e., the sequence of 6 nucleotides that lies immediately downstream from the T at −13, and/or if EBS1 sequence of the aI2 intron RNA does not have substantial complementarity to the IBS1 sequence, i.e., the sequence of six nucleotides that lie immediately downstream of the IBS2 sequence and immediately upstream of the T at +1, then the EBS1 sequence and EBS2 sequence of the group II intron RNA are modified to have substantial complementarity, as hereinafter explained. The aI2 nucleotide integrase cleaves both strands of the substrate with greater efficiency if the top strand of the substrate has an A at −21, a G at −19, a C at −18, a G at −16, a T at −15, a T at −13, a T at +1, a T at +4, and a G at +6. The aI2 cleaves both strands of the substrate with even greater efficiency if the top strand has an A at −21, a T at −20, a G at −19, a C at −18, −a T at −17, a G at −16, a T at −15, a T at −13 a T at +1, a T at +4, and a G at +6. If the top strand of the substrate additionally has a C at +2, a T at +3, a T at +7, an A at +8, an A at +9, and a T at +10, cleavage will be even greater.

The aI1 integrase is used to cleave both strands of a DNA substrate that has on the top strand thereof a C residue at position −13 relative to the cleavage site a T at +1, a T at +2, a T at +3, a T at +4, an A at +5, a G at +6, a T at +7, and an A at +8 relative to the cleavage site. Preferably, the top strand of the double-stranded substrate has a C at −13, a G at −22, a G at −21, an A at −19 a T at +1, a T at +2, a T at +3, a T at +4, an A at +5, a G at +6, a T at +7, and an A at +8. Cleavage is more efficient if there is a G at −22, a G at −21, an A at −19, an A at 18, a C at −13, a T at +1, an T at +2, an T at +3, a T at +4, a A at +5, a G at +6, a T at +7, an A at +8, a G at +9, and a T at +10 on the top strand of the DNA substrate. If the top strand of the substrate additionally comprises a T at −20, a T at −17, a T at −16, a C at −15, and an A at −14, cleavage will be even greater.

The ltrA nucleotide integrase is used to cleave both strands of a double-stranded DNA substrate, when the substrate has on the top strand thereof a G at −21, an A at −20 a C +1, an A at +2, a T at +3, an A at +4, a T at +5, a C at +6, an A at +7, and a T at +8. The ltrA nucleotide integrase cleaves both strands of the substrate more efficiently if the top strand has a G at −21, an A at −20, a T at −19, a G at −17, and G at −15, a C +1, an A at +2, a T at +3, an A at +4, a T at +5, a C at +6, an A at +7, and a T at +8. If the top strand additionally has a C at −22, a C at −18, a T at −16, an A at −14, an A at −13, a T at +9 and a T at +10, cleavage will be even greater.

Another method uses a nucleotide integrase for cleaving a single-stranded nucleic acid substrate, i.e., a single-stranded DNA or RNA, and for attaching the group II intron RNA molecule into the cleavage site. The method comprises the steps: providing a nucleotide integrase comprising: a group II intron RNA having two hybridizing sequences, EBS1 and EBS2, which are capable of hybridizing with two intron RNA-binding sequences, IBS1 and IBS2, respectively on the substrate, and a group II intron encoded protein having an RT domain, an X domain and the non-conserved portions of the Zn domain; and reacting the substrate with the nucleotide integrase. The EBS1 sequence of the group II intron RNA comprises from about 5 to 7 nucleotides and has at least 80%, preferably 90%, and more preferably full complementarity with the nucleotides at positions −1 to about −5 or about −7. The EBS2 sequence of the group II intron RNA comprises 4 to 7 nucleotides and has at least 80%, preferably 90%, more preferably full complementarity with the nucleotides at positions from about −6 to about −14. Preferably, the nucleotide immediately preceding the first nucleotide of EBS1 is complementary to the nucleotide at +1 in the sense strand.

The present invention also provides a method of determining whether a nucleic acid substrate comprises a particular recognition site. The method comprises the steps of providing a nucleotide integrase capable of cleaving a nucleic acid substrate with a particular recognition site; reacting the nucleotide integrase with the nucleic acid substrate; and assaying for cleavage of the substrate. Cleavage of the substrate indicates that the substrate comprises the particular recognition site. In addition to assaying for fragmentation and alterations in size of the nucleic acid substrate, cleavage may be detected by assaying for incorporation into or attachment of the group II intron RNA to one strand of the nucleic acid substrate.

While a wide range of temperatures are suitable for the methods herein, good results are obtained at a reaction temperature of from about 30° C. to about 42° C., preferably from about 30° to about 37° C. A suitable reaction medium contains a monovalent cations such as $Na^+$ or $K^+$, at a concentration from about 0 to about 300 mM; preferably from about 10 to about 200 mM KCl, and a divalent cation, preferably a magnesium or manganese ion, more preferably a magnesium ion, at a concentration that is less than 100 mM and greater than 1 mM. Preferably the divalent cation is at a concentration of about 5 to about 20 mM, more preferably about 10 to about 20 mM. The preferred pH for the medium is from about 6.0–8.5, more preferably about 7.5–8.0.

In the above-described methods it is believed that the single stranded nucleic acid substrates and the top strand of the double-stranded DNA substrate are cut by the excised group II intron RNA. The cleavage that is catalyzed by the excised group II intron RNA is a reverse splicing reaction that results in the insertion, either partially or completely, of the excised group II intron RNA into the cleavage site, i.e. between nucleotides −1 and +1 in the top strand. During partial insertion the group II intron RNA is covalently attached to the +1 nucleotide on the top strand of the cleavage site. It is believed that the bottom strand or antisense strand of the double-stranded DNA substrate is cut by the group II intron-encoded protein. The bottom strand of the double-stranded DNA substrate is cut at a position from about 9 to about 11 base pairs downstream of the cleavage site in the top strand, i.e., at a site between nucleotide positions +9, +10, and +11.

The methods of using a nucleotide integrase as an endonuclease to cleave a substrate DNA are useful analytical tools for determining the presence and location of a particular recognition site in a DNA substrate. Moreover, the simultaneous insertion of a nucleic acid molecule into the DNA substrate, which occurs when either single-stranded DNA or double-stranded DNA is cleaved with a nucleotide integrase, permits tagging of the cleavage site of the DNA substrate with a radiolabeled molecule, a feature which facilitates in identifying DNA substrates that contain a particular recognition site. In addition, the automatic attachment of an RNA molecule onto one strand of a double-stranded DNA substrate permits identification of the cleavage site through hybridization studies that use a probe that is complementary to the attached RNA molecule. An attached RNA molecule that is tagged with a molecule such as biotin also enables the cleaved strand to be affinity purified.

The methods of using nucleotide integrases to cleave RNA and DNA substrates having a recognition site are useful for rendering certain genes within the substrates nonfunctional. Such methods are also useful for inserting a nucleic acid into the cleavage site, thus, changing the characteristics of the RNA molecules and the protein molecules encoded by the substrates.

The nucleotide integrase

The nucleotide integrase is a ribonucleoprotein ("RNP") particle and comprises a group II intron encoded RNA and a group II intron encoded protein, which protein is bound to the RNA. Preferably, the group II intron RNA is an excised group II intron RNA. "Excised group II intron RNA," as used herein, refers to an RNA that is either an in vitro or in vivo transcript of the DNA of the group II intron and that lacks flanking exon sequences. The excised group II intron RNA is obtained from wild type organisms, or mutated organisms, by in vivo transcription and splicing, or by in vitro transcription and splicing from the transcript of a modified or unmodified group II intron. "Group II intron encoded protein" as used herein, is a protein encoded by a group II intron open reading frame.

Group II introns are a specific type of intron which is present in the DNA of bacteria and in the DNA of organelles, particularly the mitochondria of fungi, yeast and plants and the chloroplast of plants. The group II intron RNA molecules, that is, the RNA molecules which are encoded by the group II introns, share a similar secondary and tertiary structure. FIG. 2 depicts the secondary structure of the aI1 and aI2 intron RNA and part of the nucleotide sequence of the wild-type aI1 and aI2 intron RNA. The group II intron RNA molecules typically have six domains. Domain IV of the group II intron RNA contains the nucleotide sequence which encodes the "group II intron encoded protein."

Nucleotide integrases include, for example, excised group II intron RNA molecules having a sequence which is identical to a group II intron RNA that is found in nature, i.e. a wild-type group II intron RNA, and excised group II intron RNA's which have a sequence different from a group II intron RNA that is found in nature, i.e. a modified, excised group II intron RNA molecule. Modified excised group II intron RNA molecules, include, for example, group II intron RNA molecules that have nucleotide base changes or additional nucleotides in the internal loop regions of the group II intron RNA, preferably the internal loop region of domain IV and group II intron RNA molecules that have nucleotide base changes in the hybridizing regions of domain I. Nucleotide integrases in which the group II intron RNA has nucleotide base changes in the hybridizing region, as compared to the wild type, typically have altered specificity for the substrate DNA of the nucleotide integrase.

The group II intron-encoded protein of the nucleotide integrase comprises an X domain and a Zn domain. The X domain of the protein has a maturase activity. The Zn domain of the protein has $Zn^{2+}$ finger-like motifs. Preferably, the group II intron-encoded protein further comprises a reverse transcriptase domain. As used herein, a group II intron-encoded protein includes modified group II intron-encoded proteins that have additional amino acids at the N terminus, or C terminus, or alterations in the internal regions of the protein as well as wild-type group II intron-encoded proteins. It is believed that the group II intron-encoded protein is bound to 3' region of the group II intron RNA.

The nucleotide integrase are provided in the form of RNP particles isolated from wild-type, mutant, or genetically-engineered organisms. The nucleotide integrase are also provided in the form of reconstituted RNP particles isolated from a reconstituted RNP particle preparation. The nucleotide integrase also comprises reconstituted RNP particles that are formed by combining an exogenous synthetic, excised group II intron RNA with either a group II intron-encoded protein or an RNA-protein complex preparation. The exogenous RNA includes both unmodified and modified group II intron RNA molecules. Preferably, the exogenous RNA is an in vitro transcript or a derivative of an in vitro transcript of an unmodified or modified group II intron. For example, the exogenous RNA may be derived by splicing from an in vitro transcript. The RNA-protein complex preparation contains group II intron-encoded protein molecules complexed to RNA molecules that are not an excised group II RNA molecule having a sequence which encodes this protein. The group II intron-encoded protein of the RNA-protein complex is associated with either a ribosomal RNA molecule, an mRNA molecule, or an excised group II intron RNA that does not encode the group II-intron encoded protein.

The nucleotide integrase may be used as a purified RNP particle or a purified reconstituted particle. Alternatively, the nucleotide integrase may be used in a partially-purified preparation which contains the RNP particles and reconstituted particles that have nucleotide integrase activity as well as other RNP particles, such as for example ribosomes. This partially-purified preparation is free of organelles.

Preparation of the Nucleotide Integrase

The nucleotide integrase is isolated from wild type or mutant yeast mitochondria, fungal mitochondria, plant mitochondria, chloroplasts, the proteotobacterium *Azotobacter vinelandii*, the cyanobacterium Calothrix, and *Escherichia coli lactococcus lactis*. The procedure for isolating the RNP particle preparation involves mechanically and/or enzymatically disrupting the cell membranes and/or cell walls of the organisms. In the case of fungi and plants, the purification also involves separating the specific organelles, such as mitochondria or chloroplasts, from the other cellular components by differential centrifugation and/or flotation gradients and then lysing the organelles with a nonionic detergent, such as Nonidet P-40. The organelle and bacterium lysates are then centrifuged through a sucrose cushion to obtain the ribonucleoprotein (RNP) particle preparation. The RNP particles may be further purified by separation on a sucrose gradient, or a gel filtration column, or by other types of chromatography.

The nucleotide integrase is also isolated from reconstituted RNP particle preparations that are prepared by combining an RNA-protein complex preparation with an exogenous, excised group II intron RNA. The RNA-protein complex preparation is preferably isolated from a yeast, fungi, or bacterium using the protocol for RNP particles described above. The RNA-protein complex preparation comprises group II intron-encoded protein molecules complexed with RNA molecules that are not an excised group II intron RNA having a sequence that encodes the group II intron-encoded protein. The group II intron-encoded protein of the RNA-protein complex preparation is associated with either a ribosomal RNA molecule, an mRNA molecule, or an excised group II intron RNA that does not encode the group II-intron encoded protein.

The exogenous RNA preferably is a synthetic molecule made by in vitro transcription or by in vitro transcription and self-splicing of the group II intron. The exogenous RNA may also be made by isolation of the group II intron RNA from cells or organelles in which it is naturally present or from cells in which an altered intron has been inserted and expressed. The exogenous RNA is then added to a preparation containing the RNA-protein complex. Preferably, the exogenous group II intron RNA is first denatured. The exogenous RNA is added to the RNA-protein complex on ice.

In another embodiment, the nucleotide integrase is made by introducing an isolated DNA molecule which comprises a group II intron DNA sequence into a host cell. Suitable DNA molecules include, for example, viral vectors, plasmids, and linear DNA molecules. Following introduction of the DNA molecule into the host cell, the group II intron DNA sequence is expressed in the host cell such that excised RNA molecules encoded by the introduced group II intron DNA sequence and protein molecules encoded by introduced group II intron DNA sequence are formed in the cell. The excised group II intron RNA and group II intron-encoded protein are combined within the host cell to produce the nucleotide integrase.

Preferably the introduced DNA molecule also comprises a promoter, more preferably an inducible promoter, operably linked to the group II intron DNA sequence. Preferably, the DNA molecule further comprises a sequence which encodes a tag to facilitate isolation of the nucleotide integrase such as, for example, an affinity tag and/or an epitope tag. Preferably, the tag sequences are at the 5' or 3' end of the open reading flame sequence. Suitable tag sequences include, for example, sequences which encode a series of histidine residues, the Herpes simplex glycoprotein D, i.e., the HSV antigen, or glutathione S-transferase. Typically, the DNA molecule also comprises nucleotide sequences that encode a replication origin and a selectable marker. Optionally, the DNA molecule comprises sequences that encode molecules that modulate expression, such as for example T7 lysozyme.

The DNA molecule comprising the group II intron sequence is introduced into the host cell by conventional methods, such as, by cloning the DNA molecule into a vector and by introducing the vector into the host cell by conventional methods, such as electroporation or by $CaCl_2$-mediated transformation procedures. The method used to introduce the DNA molecule is related to the particular host cell used. Suitable host cells are those which are capable of expressing the group II intron DNA sequence. Suitable host cells include, for example, heterologous or homologous bacterial cells, yeast cells, mammalian cells, and plant cells. In those instances where the host cell genome and the group II intron DNA sequence use different genetic codes, it is preferred that the group II intron DNA sequence be modified to comprise codons that correspond to the genetic code of the host cell. The group II intron DNA sequence, typically, is constructed de novo from synthetic oligonucleotides or modified by in vitro site-directed mutagenesis to prepare a group II intron DNA sequence with different codons. Alternatively, to resolve the differences in the genetic code of the intron and the host cell, DNA sequences that encode the tRNA molecules which correspond to the genetic code of the group II intron are introduced into the host cell. Optionally, DNA molecules which comprise sequences that encode factors that assist in RNA or protein folding, or that inhibit RNA or protein degradation are also introduced into the cell.

The DNA sequences of the introduced DNA molecules are then expressed in the host cell to provide a transformed host cell. As used herein the term "transformed cell" means a host cell that has been genetically engineered to contain additional DNA, and is not limited to cells which are cancerous. Then the RNP particles having nucleotide integrase activity are isolated from the transformed host cells.

Preferably, the nucleotide integrase is isolated by lysing the transformed cells, such as by mechanically and/or enzymatically disrupting the cell membranes of the transformed cell. Then the cell lysate is fractionated into an insoluble fraction and soluble fraction. Preferably, an RNP particle preparation is isolated from the soluble fraction. RNP particle preparations include the RNP particles having nucleotide integrase activity as well as ribosomes, mRNA and tRNA molecules and other RNPs. Suitable methods for isolating RNP particle preparations include, for example, centrifugation of the soluble fraction through a sucrose cushion. The RNP particles, preferably, are further purified from the RNP particle preparation or from the soluble fraction by, for example, separation on a sucrose gradient, or a gel filtration column, or by other types of chromatography. For example, in those instances where the protein component of the desired RNP particle has been engineered to include a tag such as a series of histidine residues, the RNP particle may be further purified from the RNP particle preparation by affinity chromatography on a matrix which recognizes and binds to the tag. For example, NiNTA Superflow from Qiagen, Chatsworth Calif., is suitable for isolating RNP particles in which the group II intron-encoded protein has a $His_6$ tag.

The following methods for preparing nucleotide integrases are included for purposes of illustration and are not intended to limit the scope of the invention.

FORMULATIONS

The RNP particle preparations of the following formulations 1–10, and the RNA-protein complex of the formulation 12 were isolated from the mitochondria of the wild-type *Saccharomyces cerevisiae* yeast strain ID41-6/161 MaTa adel lys1, hereinafter designated "161", and derivatives thereof. The mitochondria of the wild-type yeast strain 161 contains a COX1 gene that includes the group II intron aI1 and the group II intron aI2.

The COX1 gene in the mutant yeast strains either lacks one of the group II introns or has a mutation in one of the group II introns. The excised group II intron RNA molecules and the group II intron encoded proteins are derived from the group II introns aI1 and aI2 that are present in the wild-type and mutant yeast strains.

The intron composition of the COX1 gene in the different yeast strains is denoted by a convention in which a superscript "+" indicates the presence of the aI1 intron or the aI2 intron, a superscript "0" indicates the absence of the aI1 or aI2 intron, and other superscripts refer to specific alleles or mutations in the aI2 intron.

Formulation 1

An RNP particle preparation was isolated from the mitochondria of the *Saccharomyces cerevisiae* wild-type yeast strain 161. The intron composition of the COX1 gene of the wild-type strain is $1^+2^+$. The RNP particle preparation contains an RNP particle that is derived from the aI1 intron and includes an excised aI1 RNA bound to a protein encoded by aI1. The preparation also contains an RNP particle that is derived from the aI2 intron and that comprises a excised aI2 RNA molecule and an associated aI2-encoded protein.

To prepare the RNP particle preparation, the yeast were inoculated into a 1 liter liquid culture medium containing 2% raffinose, 2% BactoPeptone from Difco and 1% yeast extract from Difco to an $O.D._{595}$ of 1.6–1.7. The cell walls were digested with 40 mg of the yeast lytic enzyme from ICN, and the cells broken by mechanical disruption with glass beads. The nuclei and cell debris were pelleted from the lysate by centrifugation for 5 minutes in a Beckman GSA rotor at 5,000 rpm. The supernatant was removed and centrifuged in a Beckman GSA rotor at 13,000 rpm for 15 minutes to obtain a mitochondrial pellet. The mitochondria were layered on a flotation gradient consisting of a 44% sucrose solution layer, a 53% sucrose solution layer, and a 65% sucrose solution layer and centrifuged in a Beckman SW28 rotor at 27,000 rpm for 2 hours and 10 minutes. The mitochondria were collected from the 53%/44% interface and suspended in buffer containing 0.5 M KCl, 50 mM $CaCl_2$, 25 mM Tris-HCl, pH 7.5, 5 mM DTT and lysed by the addition of Nonidet P-40 to a final concentration of 1%. The mitochondrial lysate was then centrifuged in a Beckman 50 Ti rotor at 50,000 rpm for 17 hours through a 1.85 M sucrose cushion in a buffer containing 0.5 M KCl, 25 mM $CaCl_2$, 25 mM Tris-HCl, pH 7.5, 5 mM DTT, to obtain a pellet of RNP particles that were largely free of mitochondrial proteins. The isolated RNP particles were resuspended in 10 mM Tris-HCl, pH 8.0 and 1 mM DTT and stored at −70° C. The preparation may be repeatedly thawed and frozen before use.

Formulation 1*a* Purified RNP particle 2.5 $O.D._{260}$ of the RNP particles from formulation 1 in a volume of 150 μl were layered onto a 12 ml 5–20% linear sucrose gradient in a buffer consisting of 100 mM KCl, 2 mM $MgCl_2$, 50 mM Tris-HCl, pH 7.5, and 5 mM DTT. The gradient was centrifuged in an SW41 rotor at 4° C. at 40,000 rpm for five hours. The gradient was fractionated into 35 fractions of approximately 0.325 ml. Fractions 12–20 contain the purified RNP particles which are substantially free of ribosomal RNA. The location of the RNP particles in the gradient fractions was independently verified by Northern hybridization with aI2 antisense RNA. The location of the small and large subunits of ribosomal RNA in the gradient fractions was independently verified by ethidium bromide staining of the fractions on a 1% agarose gel. Approximately 85% of the ribosomal RNA is found in a fraction that does not contain the RNP particles which comprise the nucleotide integrase.

Formulation 2 RNP particle preparation from mutant yeast strain $1°2^{+r}$

The RNP particles comprise an excised aI2 RNA and an aI2-encoded protein. Yeast strain $1°2^{+r}$ was obtained from Dr. Philip S. Perlman at the University of Texas Southwestern Medical Center and was prepared as described in Moran et al., 1995, *Mobile Group II Introns of Yeast Mitochondrial DNA Are Novel Site-Specific Retroelements*, Mol. Cell Biol. 15, 2828—38, which is incorporated herein by reference. The $1°2^{+r}$ mutant strain was constructed as follows: (i) the aI2 intron from strain 161 was cloned as a ClaI-to-BamHI fragment into pBluescript KS$^+$ obtained from Stratagene to yield pJVM4; (ii) pJVM4 was cleaved with ClaI and NdeI to remove the 5' end of the insert; and (iii) an MspI-to-NdeI fragment that contains exons 1 and 2 of the mitochondriae COX1 gene plus the 5' end of aI2 from yeast strain C1036Δ one was inserted to yield plasmid pJVM164. Yeast strain C10361Δone, in which aI1 is excised from the mitochondrial DNA, was prepared as described in Kennel et al., 1993, *Reverse transcriptase activity associated with maturase-encoding group II introns in yeast mitochondria*. Cell 73, 133–146, which is incorporated herein by reference. pJVM164 was transformed into a [rho$^0$] strain, and the $1°2^{+r}$ allele was placed into an intact mitochondrial DNA by recombination. This last step is accomplished by mating to a nonreverting COX1 mutant derived from mutant C1036 (strain 5B), whose construction is described in Kennel et al., 1993, and selecting for recombinant progeny that are capable of respiring and growing on glycerol-containing medium (GLY$^+$) and that contain the transformed COX1 allele in place of the 5B allele.

The reactions and manipulations directed at cloning DNA, such as ligations, restriction enzyme digestions, bacterial transformation, DNA sequencing etc. were carried out according to standard techniques, such as those described by Sambrook et al., *Molecular cloning: a laboratory manual*, 2nd ed., Cold Spring Harbor Laboratory Press. Cold Spring Harbor. N.Y. Yeast mitochondrial transformations were also carried out according to standard techniques such as those described in Belcher et al., 1994, Biolistic transformation of mitochondria in *Saccharomyces cerevisiae*, 101–115. In N.

-S. Yang and P. Christou (ed.) *Particle Bombardment Technology for Gene Transfer*. Oxford University Press, New York. The RNP particle preparation was made from the mitochondria of mutant yeast strain $1°2^{+r}$, as in formulation 1.

Formulation 3 RNP particle preparation from mutant yeast strain $1^{+r}2°$

Yeast strain $1^{+r}2°$ is a derivative of the wild-type yeast strain 161. The yeast strain $1^{+r}2°$ was obtained from Dr. Philip S. Perlman and was prepared as described in Kennell et al., 1993. Cell 73, 133–146. Yeast strain $1^{+r}2°$ contains a segment of the COX1 gene of *S. diastaticus*, which lacks aI2, inserted into wild-type 161 mtDNA via mitochondrial transformation. The construction started with plasmid pSH2, which contains aI1 from wild-type 161 and some flanking sequences cloned as a HpaII/EcoRI fragment in pBS(+) (Stratagene, La Jolla, Calif.). That plasmid was cleaved near the 3' end of aI1 with ClaI and in the downstream polylinker with BamHI, and the gap was filled with a ClaI/BamHI fragment from *S. diastaticus* mitochondrial DNA (NRRL Y-2416) that contains the 3' end of aI1, E2, E3 and most of aI3, thus creating a $1^{+r}2°$ form of the COX1 gene. The plasmid containing the hybrid COX1-$1^{+r}2°$ segment was transformed into a rho° derivative of strain MCC109 (MATα ade2-101 ura3-52 karl-1) by biolistic transformation. The resulting artificial petite was crossed to strain n161/m161-5B, and gly$^+$recombinants containing the COX1 $1^{+r}2°$ allele in the n161 background were isolated. The hybrid aI1 allele, which is spliced normally, differs from that of wild-type 161 by one nucleotide change, C to T, at position 2401, changing $Thr_{744}$ to Leu in the intron open reading frame. The RNP particle preparation was made from the mitochondria of mutant yeast strain $1^{+r}2°$ as in formulation 1. The RNP particles comprise an excised aI1 RNA molecule and an aI1 encoded protein.

Formulation 4 RNP particle preparation from mutant yeast strain $1°2^{YAHH}$ Yeast strain $1°2^{YAHH}$ was obtained from Dr. Philip S. Perlman and was made as described in Moran et al., 1995, Mol. Cell Biol. 15, 2838–38., using a mutagenized pJVM164 plasmid. The allele was made by oligonucleotide-directed mutagenesis of pJVM164 which contains a 4.4 kb MspI/BamHI fragment extending from 217 nucleotides upstream of exon 1 through intron aI3 of the COX1 allele. The mutagenesis changes the aI2 nucleotides 1473 to 1478 from GAT GAT to CAT CAT (D-491D-492 to HH). The RNP particles comprise a mutated, excised aI2 RNA and an aI2-encoded protein that has the mutation YADDYAHH in the reverse transcriptase domain of the protein. The RNP particle preparation was made from the mitochondria of mutant yeast strain $1°2^{YAHH}$ as in formulation 1.

Formulation 5 RNP particles from the mutant yeast strain $1°2^{P714T}$

The mutant yeast strain $1°2^{P714T}$ was obtained from Dr. Philip S. Perlman and was constructed according to the procedure described in Kennell et al., 1993, *Cell* 73, 133–146, where it is named n161/m161-C1036Δ1. The RNP particles comprise a mutated, excised aI2 intron RNA molecule and an aI2-encoded protein that carries the missense mutation $P_{714}T$ in the Zn domain. The RNP particle preparation was made from mitochondria of mutant yeast strain $1°2^{P714T}$ as in formulation 1.

Formulation 6 RNP particle from mutant yeast strain $1°2^{HHVR}$

The mutant yeast strain $1°2^{HHVR}$ was obtained from Dr. Philip S. Perlman and was made by using the nucleotide described in Moran et al., 1995, Mol. Cell Biol. 15, 2828–38, which is incorporated herein by reference, using a mutagenized pJVM164 plasmid. The allele was constructed by site-directed mutagenesis of pJVM164. The aI2 intron has the following changes: positions 2208–2219 from CAT-CACGTAAGA SEQ. ID. NO. 9 to GCAGCTGCAGCT, ($H_{736}H_{737}V_{738}R_{739}$ to AAAA) and $A_{2227}$ A to T ($N_{742}I$). This nucleotide integrase preparation comprises a mutated, excised aI2 intron RNA and an aI2-encoded protein that has a missense mutation in the HHVR motif. The RNP particle preparation was made from mitochondria of mutant yeast strain $1°2^{HHVR}$.

Formulation 7 RNP particle from mutant yeast strain $1°2^{\Delta ConZn}$

The mutant yeast strain $1°2^{\Delta ConZn}$ was obtained from Dr. Philip S. Perlman and was made as described in Moran et al., 1995, Mol. Cell Biol. 15, 2828–38, using a mutagenized pJVM164 plasmid. The allele was constructed by oligonucleotide-directed mutagenesis of pJVM164. The aI2 intron has the following changes:positions 2157–2165 changed from TTATTTAGT to TAATAATAA ($L_{719}F_{720}S_{721}$ to OchOchOch). RNP particles comprise a mutated, excised aI2 intron RNA and an aI2-encoded protein that lacks the most conserved motifs in the Zn domain. The RNP particle preparation was made from mitochondria of mutant yeast strain $1°2^{\Delta ConZn}$.

Formulation 8 RNP particle from mutant yeast strain $1°2^{C-C/1}$

The mutant yeast strain $1°2^{C-C/1}$ was obtained from Dr. Phillip S. Perlman and was made by using a nucleotide described in Moran et al., 1995 Mol. Cell Biol. 15, 2828–38, using a mutagenized pJVM164 plasmid. The allele was constructed by site-directed mutagenesis of pJVM164. The aI2 intron has the following changes:positions 2172–2173 changed from TG to GC ($C_{724}A$) and 2180–2182 changed from TTG to AGC ($I_{726}C_{727}$ to MA). The RNP particles comprise a mutated, excised aI2 intron RNA and an aI2-encoded protein that has three amino acid residues changed in the first $Zn^{+2}$-finger-like motif. The RNP particle preparation was made from mitochondria of mutant yeast strain $1°2^{C-C/1}$.

Formulation 9 RNP particles from mutant yeast strain $1°2^{C-C/2}$

The mutant yeast strain $1°2^{C-C/2}$ was obtained from Dr. Philip S. Perlman and was made as described in Moran et al., 1995 Mol. Cell Biol. 15,2828–38, using a mutagenized pJVM164 plasmid. The allele was constructed by site-directed mutagenesis of pJVM164. The aI2 intron has the following changes: position 2304–2305 changed from TG to GC ($C_{768}A$) and 2313–2314 changed from TG to GC ($C_{771}A$). The RNP particles comprise a mutated excised aI2 intron RNA and an aI2-encoded protein that has two amino acids changed in the second $Zn^{+2}$ finger-like motif. The RNP particle preparation was made from mitochondria of mutant yeast strain $1°2^{C-C/2}$.

Formulation 10 RNP particles from mutant yeast strain $1°2^{H6}$

The mutant yeast strain, obtained from Dr. Philip S. Perlman, was made by transferring the mutagenized plasmid pJVM 164 into the mitochondria of yeast strain GRF18 as described in Moran et al., 1995 Ref. The allele was constructed by site-directed mutagenesis of pJVM164 and has the sequence CATCATCATCATCATCAT, SEQ. ID. NO. 10, inserted between nucleotides 2357 and 2358 of the aI2 intron. The RNP particle preparation was made from mitochondria of mutant yeast strain $1°2^{H6}$ according to the protocol described above for formulation 1. The RNP particles comprise a mutated, excised aI2 intron RNA and an aI2-encoded protein that has six histidines added to the C terminus of the aI2-encoded protein.

Formulation 11 RNP particles from Neurospora intermedia.

Mitochondria from the Varkud strain of Neurospora intermedia, which is available from the Fungal Genetics Stock Center, were prepared as described in Lambowitz A. M. 1979, Preparation and analysis of mitochondrial ribosomes. Meth. Enzymol. 59, 421–433. The conidia were disrupted with glass beads and the mitochondria and RNP particles isolated as described in formulation 1. The RNP particles comprise an excised coI intron RNA and the protein encoded by the coI intron.

Formulation 12 Reconstituted RNP particle preparation

A reconstituted RNP particle preparation was made by incubating an exogenous, excised, in vitro RNA transcript of the aI2 intron with an RNA-protein complex preparation isolated from the mutant yeast strain $1°2^{\Delta D5}$, in which the aI2 intron RNA lacks a domain V and is therefore splicing defective. The mutant allele $1°2^{\Delta D5}$ was obtained from Dr. Philip S. Perlman and was constructed using the same procedure that was used to make yeast strain $1^+2^{\Delta D5}$ that was described in Moran et al. 1995, except that the final mating was with yeast strain $1°2^+$. The RNA-protein complex preparation was isolated from $1°2^{\Delta D5}$ using the protocol described above in formulation 1 for RNP particle preparations. The RNA-protein complex preparation isolated from the mitochondria of $1°2^{\Delta D5}$ does not contain excised aI2 RNA but does contain aI2-encoded protein that is associated with other RNA molecules in the preparation.

The exogenous RNA was made by in vitro transcription of the plasmid pJVM4 which includes a fragment of the yeast mitochondrial COX1 gene from the ClaI site of the group II intron 1 (aI1) to the BamHI site of aI3 that has been inserted into the pBLUESCRIPT KS(+) plasmid. Plasmid pJVM4 contains the following COX1 sequences: Exon 2, aI2, Exon 3 and parts of aI1 and aI3 sequence. The sequences are operably linked to a T3 RNA polymerase promoter. The Exon 2 and Exon 3 sequence are required for self-splicing of the aI2 intron RNA from the RNA transcript. pJVM4 was linearized with BstEII, which cuts at the 3' end of Exon 3 then 5 μg of the plasmid was incubated in 0.300 ml of 40 mM Tris-HCl at pH 8.0, 25 mM NaCl, 8 mM MgCl$_2$ 2 mM spermidine, 5 mM DTT 500 mM rNTPs, 600 U of RNasin from US Biochemical and 300–750 U of T3 RNA polymerase from BRL at 37° C. for 2 hours to make the RNA transcripts. Following the incubation, the RNA transcripts were phenol-CIA extracted, purified on G-50 column, phenol-CIA extracted and precipitated with ethanol. The RNA transcripts were then incubated in 40 mM Tris-HCl at pH 7.5, 100 mM MgCl$_2$, 2 M NH$_4$Cl at 40–45° C. for 1 hour to allow self-splicing of the aI2 intron RNA molecules from the RNA transcripts and to obtain the splicing products. The splicing products, which include the excised aI2 RNA transcript, the ligated transcript which lacks the aI2 intron RNA, and the unspliced transcript, were desalted by passing through a G-50 column, then phenol-CIA extracted and ethanol precipitated to provide the exogenous RNA. The exogenous RNA was then resuspended to a final concentration of 1.0 μg/μl in 10 mM Tris-HCl, pH 8.0, 1 mM EDTA.

To prepare the reconstituted RNP particle preparation, 1 μl of the exogenous RNA was added to 2 μl of the $1°2^{\Delta D5}$ RNA-protein complex preparation (0.025 O.D.$_{260}$ units) on ice for 0–10 minutes. The preparation was used immediately.

Formulation 13 Reconstituted RNP Particle Preparation containing a Nucleotide Integrase Comprising a Group II Intron RNA Having Modified EBS Sequences Plasmid pJVM4 derivatives were used to prepare exogenous aI2 intron RNA molecules in which the EBS1 and EBS2 sequences are different from the EBS sequences in the wild-type aI2 intron. pJVM4 contains the aI2 intron sequence and flanking exon sequences from wild-type yeast 161 cloned downstream of a phage T3 promoter in pBluescript II KS(+). Plasmids containing modified introns were derived from pJVM4 by PCR mutagenesis with appropriate primers. In all cases, the modified region was sequenced to verify the correct mutation and the absence of adventitious mutations.

Plasmids pJVM4-aI1EBS1, pJVM4-aI1EBS2 and pJVM4-aI1EBS1/EBS2 contain aI2 RNA derivatives in which the EBS1 and/or EBS2 sequences were replaced with those of aI1. In each case, portions of the 5' and 3' exons were also changed to aI1 sequences to permit in vitro splicing. pJVM4-aI1EBS1 has EBS1 positions 2985–2990 changed from 5'AGAAGA to 5'CGTTGA; pJVM4-aI1EBS2 has EBS2 positions 2935–2940 changed from 5'TCATTA to 5' ACAATT; and pJVM4-aI1EBS1EBS2 has EBS1 and EBS2 positions 2935–2940 and 2985–2990 changed from 5'TCATTA to 5'ACAATT and 5'AGAAGA to 5'CGTTGA, respectively. For pJVM4-aI1EBS1 and pJVM4-aI1EBS1/EBS2, the 5' portion of the pJVM4 insert consisting of aI1 and E2 sequence was replaced with the last 24 bp of E1. For pJVM4-aI1EBS2, positions −24 to −7 (GTCATGCTGTATTAATGA) SEQ. ID. NO. 11 were replaced with (ATGGTAATTCACAATTAT), SEQ. ID. NO. 12 leaving the aI2 IBS1 sequence unchanged. For all three constructs, the 3' portion of the insert was replaced by the first 15 bp of E2 instead of E3 and aI3.

pJVM4-EBS2-8G, pJVM4–EBS2-9T-10A, pJVM4-EBS2-11A, pJVM4-EBS2-12T, and pJVM4-EBS2-13T(1) are derivatives of pJVM4 in which the indicated changes were introduced at different positions in EBS2. pJVM4-EBS2-13T(2) is identical to pJVM4-EBS2-13T(1) except that it contains a second mutation, T to A, at intron position 2932.

pJVM4-δ-C, pJVM4-δ-G, and pJVM9-δ-T are derivatives of pJVM4 in which the δ nucleotide (position 2984) was changed to C, G, or T, respectively, with the compensatory nucleotide substituted at the δ position of exon 3 for in vitro splicing.

Exogenous aI2 intron transcripts having a modified EBS1 sequence and/or a modified EBS2 sequence were synthesized using phage T3 polymerase and the modified plasmids as templates. The synthetic transcripts contained regions of the modified aI2 intron RNA and regions of the flanking exon 2 and exon 3 of the yeast mitochondrial COX1 protein. The synthetic transcripts were self-spliced and the spliced products desalted through a G-50 column, phenol-CIA extracted, ethanol precipitated, and dissolved in TE (pH8.0) at a final concentration of 1.0 μg/μl (0.52 μM).

The resulting modified, excised aI2 RNA molecules were individually mixed with RNA-protein complex preparations isolated from $1°2^{\Delta D5}$ using the protocol described above in formulation 1 for RNP particle preparations. This yeast mutant has a deletion in domain V of the aI2 intron and is unable to splice aI2 RNA. This mutant overproduces aI2 protein from the unspliced precursor mRNA. Thus, the RNA-protein complex preparation contains larger amounts of the aI2 protein.

For reconstitution, 1 μl of the spliced, synthetic aI2 transcripts was mixed with 2 μl (0.025OD$_{260}$ units) of the RNA-protein complex preparation and incubated on ice for 0–10 minutes.

Formulation 14

An RNP particle preparation containing an RNP particle in which the loop region of domain IV of the group II intron RNA is modified, that is the loop region nucleotide sequence of domain IV differs from the nucleotide sequence of the aI2 RNA of formulations 1–10 is prepared by two methods. First oligonucleotide-directed mutagenesis of the aI2 intron DNA is performed by standard, well-known methods to change the nucleotide sequences which encode for the loop region of domain IV of the aI2 intron RNA. The mutagenized aI2 intron DNA is then inserted into a vector, such as a plasmid, where it is operably linked to an RNA polymerase promoter, such as a promoter for T7 RNA polymerase or SP6 RNA polymerase or T3 RNA polymerase and an in vitro transcript of the modified group II intron RNA is made as described above in formulation 12. The exogenous RNA is then combined with an RNA-protein complex that has been isolated as described for formulation 12 to produce a modified reconstituted RNP particle preparation.

Alternatively, an RNP particle preparation in which the sequences within the loop region of the group II intron RNA are modified is prepared by site-directed mutagenesis of an organism, such as a yeast, as described in formulations 4–10, and by isolation of the RNP particle preparation from the organism as described in formulation 1.

Formulation 15 RNP Particle Preparation from a Genetically-Engineered Cell

A nucleotide integrase comprising an excised RNA which is encoded by the Ll.ltrB intron of a lactococcal cojugative element pRS01 of Lactococcus lactis and the protein encoded by the ORFLtrA of the Ll.ltrB intron were prepared by transforming cells of the BLR(DE3) strain of the bacterium *Escherichia coli*, which has the recA genotype, with the plasmid pETLtrA19. Plasmid pETLtrA19 comprises the DNA sequence for the group II intron Ll.ltrB from *Lactococcus lactis*, positioned between portions of the flanking exons ltrBE1 and ltrBE2. pETLtrA19 also comprises the DNA sequence for the T7 RNA polymerase promoter and the T7 transcription terminator. The sequences are oriented in the plasmid in such a manner that the ORF sequence, SEQ. ID. NO. 6, within the Ll.ltrB intron is under the control of the T7 RNA polymerase promoter. The ORF of the Ll.ltrB intron encodes the protein ltrA. The sequence of the Ll.ltrB intron and the flanking exon sequences present in pETLtrA19 are shown SEQ.ID. NO. 5. The amino acid sequence of the ltrA protein is shown in SEQ. ID. NO.7. Domain IV is encoded by nucleotide 705 to 2572.

pETLtrA19 was prepared first by digesting pLE12, which was obtained from Dr. Gary Dunny from the University of Minnesota, with HindIII and isolating the restriction fragments on a 1% agarose gel. A 2.8 kb HindIII fragment which contains the Ll.ltrB intron together with portions of the flanking exons ltrBE1 and ItrBE2 was recovered from the agarose gel and the single-stranded overhangs were filled in with the Klenow fragment of DNA polymerase I obtained from Gibco BRL, Gaithersburg, Md. The resulting fragment was ligated into plasmid pET-11a that had been digested with XbaI and treated with Klenow fragment. pET-11A was obtained from Novagen, Madison, Wis.

pETLtrA19 was introduced into the *E. coli* cells using the conventional $CaCl_2$-mediated transformation procedure of Sambrook et al. as described in "Molecular Coning A Laboratory Manual", pages 1–82, 1989 . Single transformed colonies were selected on plates containing Luria-Bertani (LB) medium supplemented with ampicillin to select the plasmid and with tetracycline to select the BLR strain. One or more colonies were inoculated into 2 ml of LB medium supplemented with ampicillin and grown overnight at 37° C. with shaking. 1 ml of this culture was inoculated into 100 ml LB medium supplemented with ampicillin and grown at 37° C. with shaking at 200 rpm until $OD_{595}$ of the culture reached 0.4. Then isopropyl-beta-D-thiogalactoside was added to the culture to a final concentration of 1 mM and incubation was continued for 3 hours. Then the entire culture was harvested by centrifugation at 2,200×g, 4° C., for 5 minutes. The bacterial pellet was washed with 150 mM NaCl and finally resuspended in ½₀ volume of the original culture in 50 mM Tris, pH 7.5, 1 mM EDTA, 1 mM DTT, and 10% (v/v) glycerol (Buffer A). Bacteria were frozen at −70° C.

To produce a lysate the bacteria were thawed and frozen at −70° C. three times. Then 4 volumes of 500 mM KCl, 50 mM $CaCl_2$, 25 mM Tris, pH 7.5, and 5 mM DTT (HKCTD) were added to the lysate and the mixture was sonicated until no longer viscous, i.e. for 5 seconds or longer. The lysate was fractionated into a soluble fraction and insoluble fraction by centrifugation at 14,000×g, 4° C., for 15 minutes. Then 5 ml of the resulting supernatant, i.e., the soluble fraction, were loaded onto a sucrose cushion of 1.85 M sucrose in HKCTD and centrifuged for 17 hours at 4° C., 50,0000 rpm in a Ti 50 rotor from Beckman. The pellet which contains the RNP particles was washed with 1 ml water and then dissolved in 25 µl 10 mM Tris, pH 8.0, 1 mM DTT on ice. Insoluble material was removed by centrifugation at 15,000×g, 4° C., for 5 minutes. The yield of RNP particles prepared according to this method comprise the excised Ll.ltrB intron RNA and the ltrA protein.

Preparation of Substrate DNA

Figure 3:
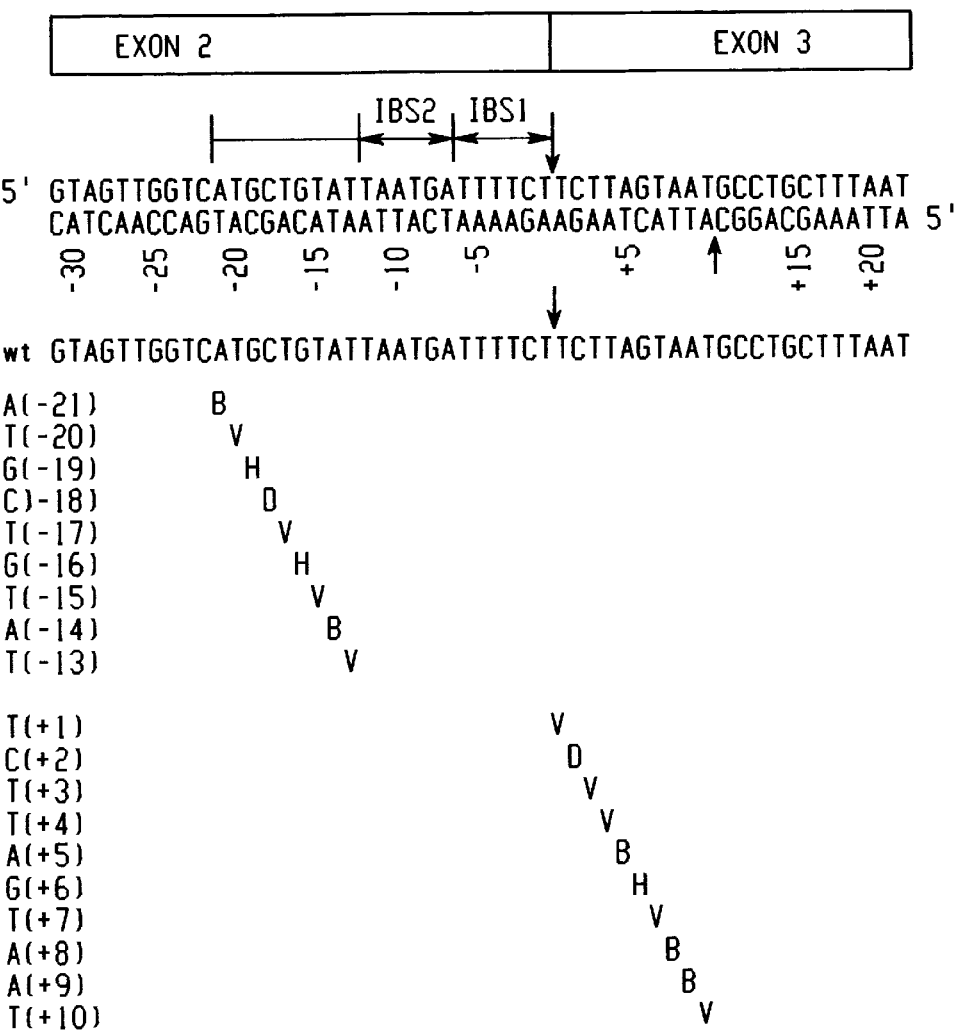
FIG. 3 is a chart depicting the sequence of a DNA substrate cleaved by a nucleotide integrase comprising a wild-type aI2 intron RNA and the protein encoded thereby and the position of the point mutations made in this sequence.
Figure 6:
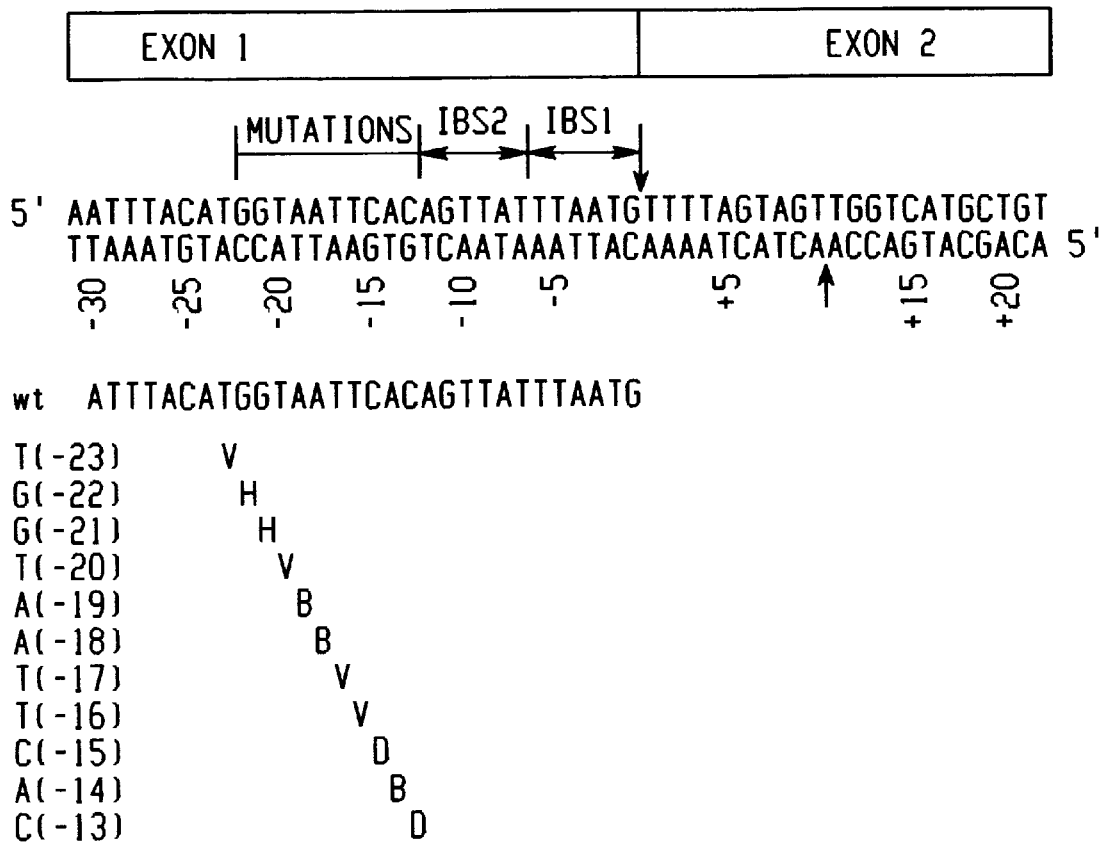
FIG. 6 is a chart depicting the sequence of a DNA substrate cleaved by a nucleotide integrase comprising a wild-type aI1 intron RNA, and the protein encoded by the aI1 intron RNA and the position of the mutations made in this sequence.
Figure 7:
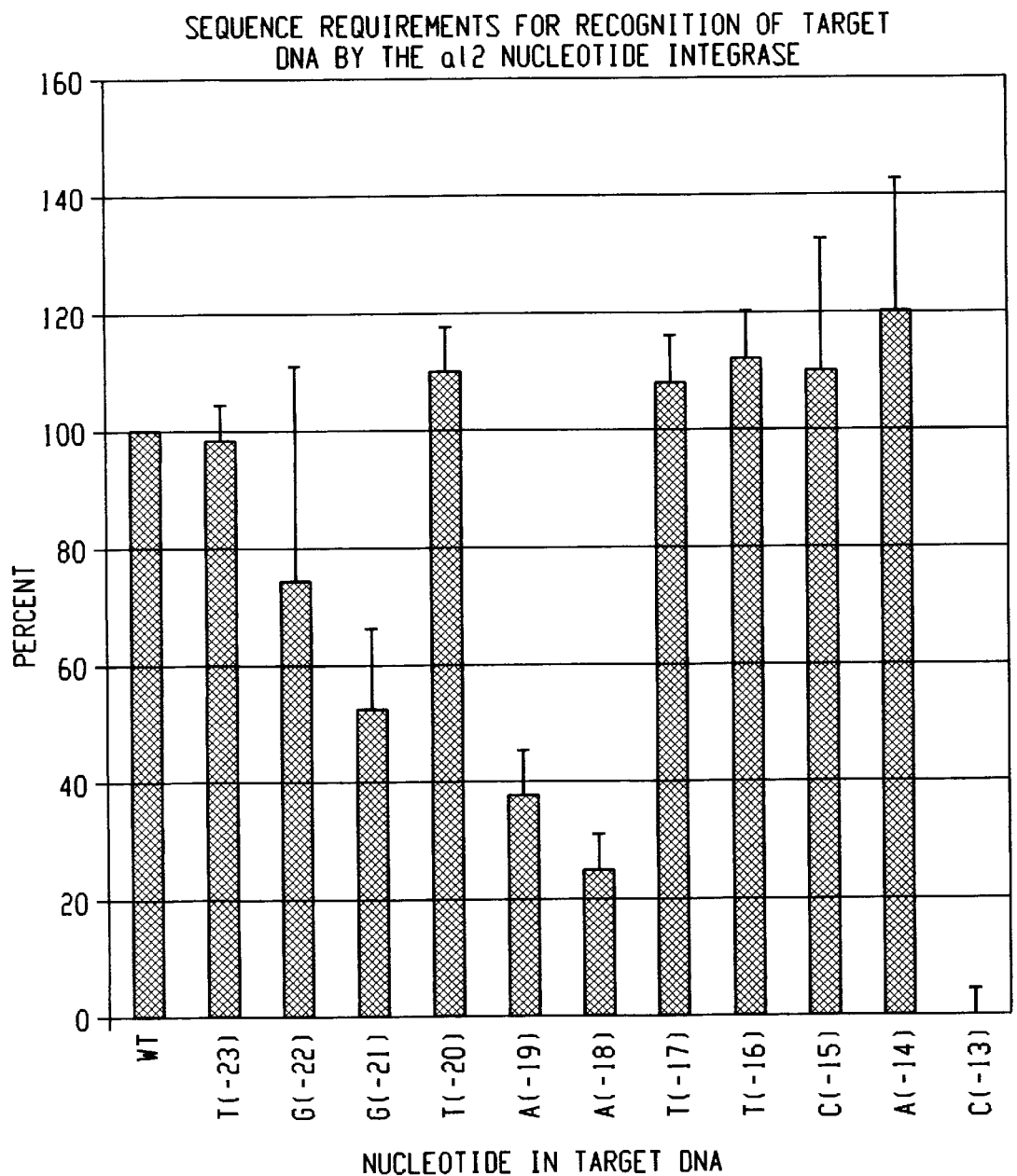
FIG. 7 is a graph showing the relative extent of cleavage of the substrates having mutations upstream of the cleavage site by a nucleotide integrase comprising a wild-type aI1 intron RNA and the protein encoded thereby.
Figure 8:
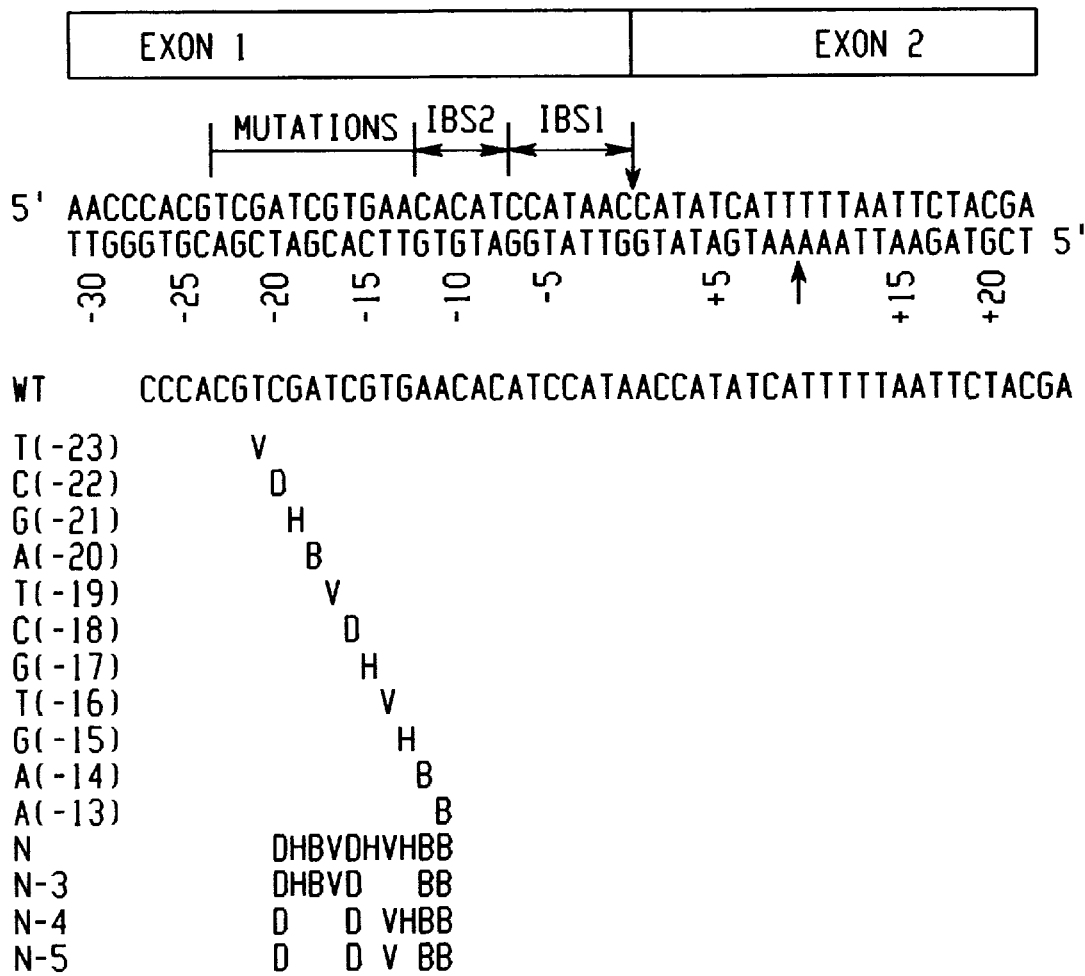
FIG. 8 is a chart depicting the sequence of a DNA substrate cleaved by a nucleotide integrase comprising a wild-type group II intron RNA of the Lactococcus lactis ltrB gene, hereinafter referred to as the "Ll.ltrB intron" RNA, and the protein encoded thereby, hereinafter referred to as the ltrA protein.
Figure 9:
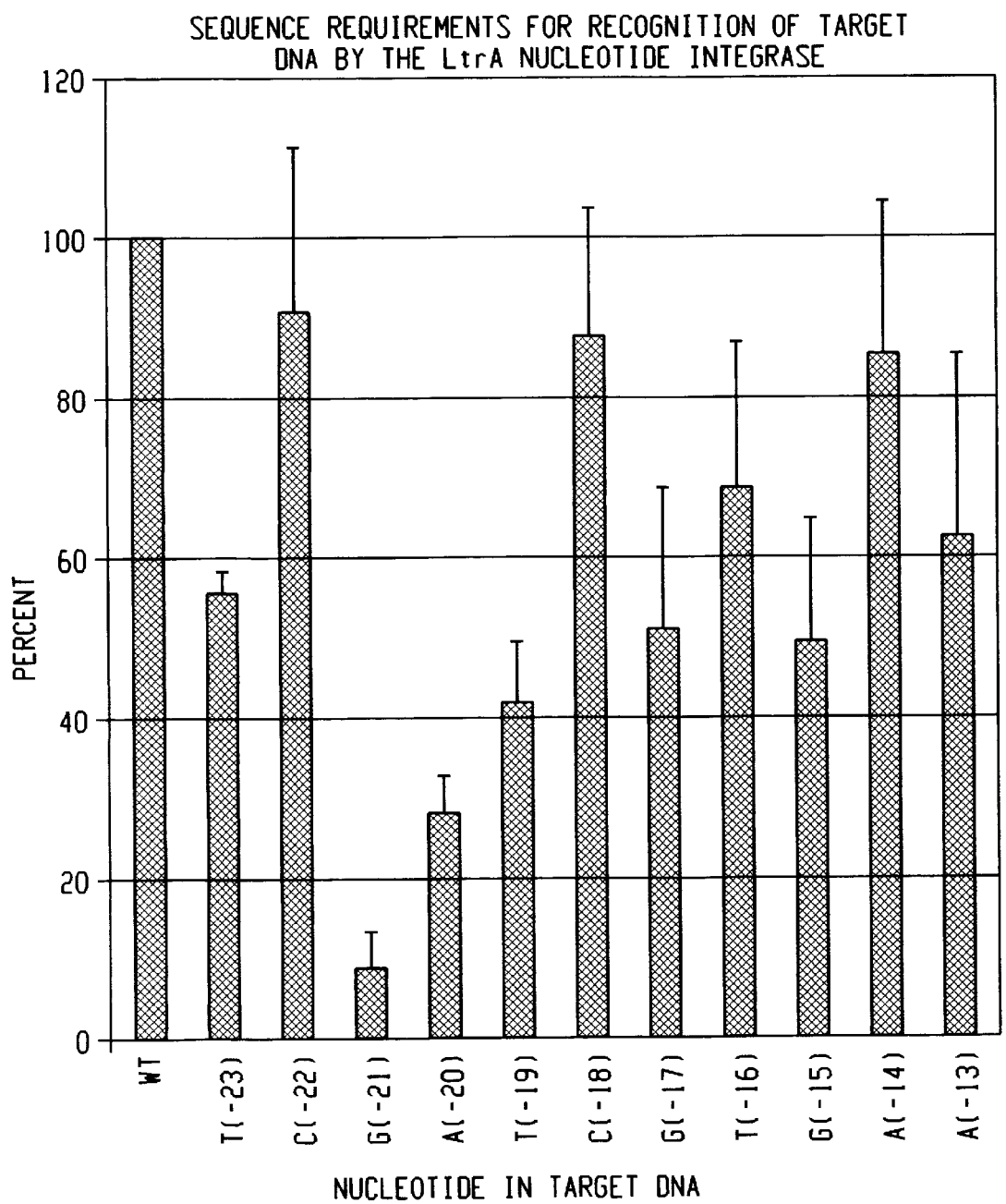
FIG. 9 is a graph showing the relative extent of cleavage of the substrates having mutations in the first sequence element by a nucleotide integrase comprising a wild-type Ll.ltrB intron RNA and the ltrA protein.

Labeled DNA substrates having sequences from the E2/E3 junction of the yeast mitochondrial COX1 gene, the E1/E2 junction of the yeast mitochondrial COX1 gene, and the E1/E2 junction of the putative Lactococcus lactis relaxase gene (ltrB) were synthesized from recombinant plasmids or synthetic oligonucleotide templates by PCR or primer extension. The sequence of the substrate containing the E2/E3 junction of the yeast mitochondrial COX 1 gene is depicted in FIG. 3 as the wt sequence. FIG. 3 also identifies the locations of the mutations in this sequence. The sequence of the substrate containing the E1/E2 junction of the yeast mitochondrial COX 1 gene is depicted in FIG. 6, which also identifies the locations of the mutations in this sequence. The sequence of the substrate containing the E1/E2 junction of the putative Lactococcus lactis relaxase gene (ltrB) is depicted in FIG. 8, which also identifies the locations of the mutations in this sequence. DNA substrates that were labeled on the 5' end of the antisense strand were also generated from plasmids by PCR with 200 ng of the 5' end-labeled primer and unlabeled primer, both of which are complementary to a sequence in the polylinker. Single-stranded DNA substrates were synthesized by end-labeling nucleotides. Short segments of double-stranded DNA substrates were also prepared The following examples of methods employing nucleotide integrases comprising an excised aI2 intron RNA bound to an aI2 protein, an excised aI1 intron RNA bound to an aI1 protein, or an excised ltrA intron RNA bound to an ltrA protein to cleave DNA substrates are for illustration only and are not intended to limit the scope of the invention.

EXAMPLE 1

Cleaving a Double-Stranded DNA Substrate with a Nucleotide Integrase Comprising a Wild-type aI2 Intron RNA and a Wild-type aI2-Encoded Protein 0.025 $O.D._{260}$ units of the RNP particles of formulation 1 were reacted with a DNA substrate consisting of yeast mitochondrial COX1 exons 2 and 3 (E2E3) and comprising the WT sequence shown in FIG. 3. The reaction was conducted at 37° C. in a buffer containing 100 mM KCl, 20 mM $MgCl_2$ at pH7.5. One portion of the cleavage products was denatured with glyoxal and analyzed in a 1% agarose gel to determine the extent of cleavage of the top strand or sense strand of the DNA substrate at the E2/E3 junction. Another portion of the nucleic acid cleavage products was analyzed in a denaturing 6% polyacrylamide gel to determine the extent of cleavage of both strands of the double stranded DNA substrate. The gels were dried and autoradiographed or quantitated by phosphorimaging with a Molecular Dynamics Phosphorimager 445.

The results indicated that the nucleotide integrase comprising an excised aI2 intron RNA from wild-type yeast bound to an aI2 intron-encoded protein from wild-type yeast cleaved the top strand of a substrate having the wt target sequence at the position marked by the arrowhead in FIG. 3. The results also indicated that the group II intron RNA is integrated into the cleavage site of the sense strand. The results also indicated that the nucleotide integrase cleaved the bottom strand or antisense strand of the double-stranded DNA substrate at a location base pairs downstream from the cleavage site in the first strand.

0.025 $O.D._{260}$ units of the RNP particles of formulation 1 were reacted with six different derivatives of the wt DNA substrate of FIG. 3. Each of the derivatives contained a single point mutation in IBS2 of the wt sequence shown in FIG. 3. In the derivatives, the nucleotides in the −7, −8, −9, −10, −11, −12, and −13 were each changed to its complement. The reactions were conducted as and the cleavage products assayed on a 1% agarose gel as described above. The results indicated that the ability of this nucleotide integrase to cleave a double-stranded DNA substrate was considerably reduced unless there was full complementarity between each of the nucleotides of EBS2 of the aI2 intron RNA and each of the nucleotides of the IBS2 of the substrate. The only exception occurred with the substrate having a mutation at the nucleotide at +7.

0.025 $O.D._{260}$ units of the nucleotide integrase of formulation 1 were reacted with derivatives of the wt DNA substrate of FIG. 3 in which the nucleotides at each of the positions from −14 to −21 in the wt sequence were separately changed to a mixture of the incorrect nucleotides. Thus, the nucleotide integrase was reacted with 10 different substrates, each of which contained a mixture of three mutations at a single site. The reactions were conducted as described above in example 1 and the cleavage products were glyoxylated and assayed on a 1% agarose gel. The results indicated that the nucleotide integrase cleaved substrates having point mutations at position −21, −20, −17, and −14 in the target sequence at levels that ranged from 67% to 115% of the levels achieved when the nucleotide integrase was reacted with the wt sequence depicted in FIG. 3. The levels of cleavage were reduced to the greatest extent with the substrates having point mutations at −15 and −18. The level of cleavage that occurred with substrates having mutations at −15 and −18 was 9% and 3% of the cleavage obtained when the nucleotide integrase was reacted with the wt sequence depicted in FIG. 3. Mutations at positions −16 and −19 had moderate effects, and substrates containing these mutation were cleaved by the nucleotide integrase at levels that were 23% and 31% of the levels achieved with a substrate having the wt sequence.

0.025 $O.D._{260}$ units of the nucleotide integrase of formulation 1 were reacted with derivatives of the DNA substrate of FIG. 3 in which the nucleotides at each of the positions from +1 to +10 in the wt sequence were separately changed to a mixture of three different bases. Thus, the nucleotide integrase was reacted with 30 different substrates, each of which had a mixture of the three different nucleotides. The reactions were conducted as described above in example 1 and the cleavage products were assayed on a 6% polyacrylamide gel to determine whether the nucleotides at these positions are required for cleavage of the antisense strand of the substrate containing the wt sequence. The cleavage products were also glyoxylated and analyzed on a 1% agarose gel to determine if changes in the nucleotides at these positions had any effect on the ability of the nucleotide integrase to cleave the top strand of the substrate. The results indicated that the aI2 nucleotide integrase cleaved substrates for the second strand having changes at position +1, +4, and +6 at levels that were 39, 33, and 29%, respectively of the levels achieved when the nucleotide integrase was reacted with the wt sequence depicted in FIG. 3. Changes in the nucleotides at the other positions, i.e., +2, +3, +5, +7, +8, +9, and +10 had little effect on the ability of the nucleotide sequence to cleave the second strand of the substrate. The results also indicated that changes in the nucleotides at each of these positions had little effect on the ability of the nucleotide integrase to cleave the top strand of the mutated substrate.

Comparative Example A 0.025 $O.D._{260}$ units of the RNP particle preparations of formulations 1, 2, 4, 5 were reacted for 20 minutes with 125 finoles (150,000 cpm) an internally-labeled DNA substrate having the wt sequence depicted in FIG. 3. To verify cleavage, the products were glyoxalated and analyzed in a 1% agarose gel. The results indicated that nucleotide integrases which lack excised aI2 intron RNA or in which the intron-encoded protein lacks the nonconserved portion of the Zn domain, will neither cleave the double-stranded DNA substrate nor attach an RNA.

EXAMPLE 2

Cleaving a Double-stranded DNA substrate with the Reconstituted RNP Particle Preparation of Formulation 12

Figure 4:
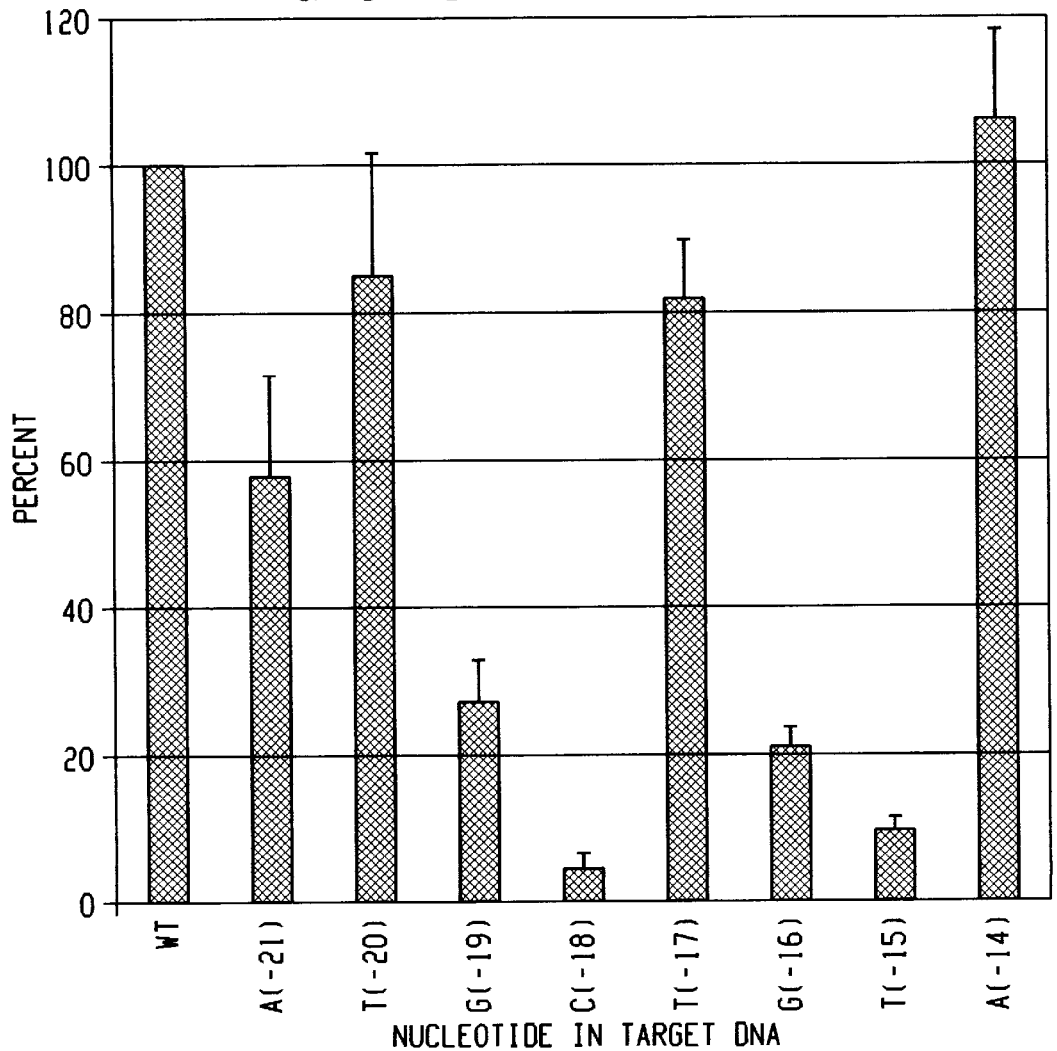
FIG. 4 is a graph showing the relative extent of cleavage of the substrates having mutations in the first sequence element by a nucleotide integrase comprising a wild-type aI2 intron RNA and the protein encoded thereby.
Figure 5:
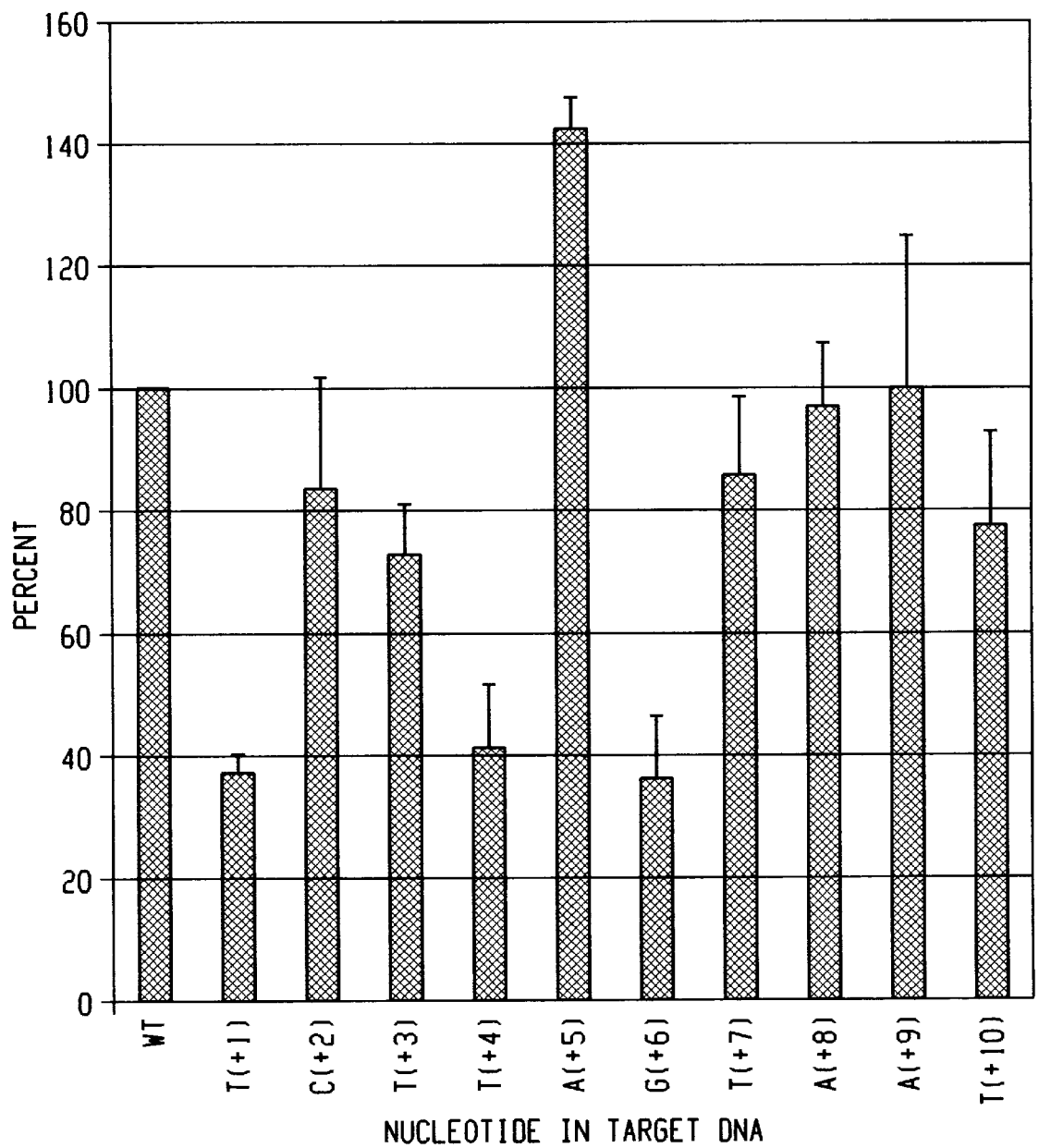
FIG. 5 is a graph showing the relative extent of cleavage of the substrates having mutations in the second sequence element by a nucleotide integrase comprising a wild-type aI2 intron RNA and the protein encoded by the aI2 intron RNA.

The reconstituted RNP particle preparation of formulation 12 was reacted with 250 fmoles (300,000 cpm) of the 142 base pair DNA substrates generated from pE2E3 and which were 5' end-labeled on either the sense strand or the antisense strand for 20 minutes at 37° C. To verify cleavage of both strands of the substrate, the reaction products were extracted with phenol-CIA in the presence of 0.3 M NaOAc and 2 µg single-stranded salmon sperm DNA followed by precipitation with ethanol. Reactions products were analyzed in a 6% polyacrylamide/8 M urea gel. The results indicated that the reconstituted particle preparation cleaves both strands of a double-stranded DNA substrate which contains the wild-type sequence shown in FIG. 4. Similar results, i.e. cleavage of both strands, were obtained when the 5' end labeled substrates were incubated with the RNP particle preparation of formulation 10.

EXAMPLE 3

Cleaving Double-stranded DNA Substrates with a Nucleotide Integrase Comprising a Modified aI2 Intron RNA and an aI2-Encoded Protein 0.025 $O.D._{260}$, units of the RNP particles of formulation 13 in which the EBS1 of the aI2 group II intron RNA was changed to the EBS1 sequence of the aI1 intron RNA was reacted with the wt DNA substrate of FIG. 3 and with a derivative thereof in which the nucleotides at position −1 to −6 were simultaneously changed to 5'TTAATG, which is the IBS1 sequence of the wt sequence for the aI1 nucleotide integrase. The reactions were conducted and the cleavage products analyzed as described in example 1. The results indicated that an aI2 nucleotide integrase comprising a group II intron RNA with a modified EBS1 was not able to cleave a substrate with the wt sequence but was able to cleave a substrate in which the nucleotides at position −1 to −6 were complementary to the modified EBS1.

EXAMPLE 4

Cleaving Substrate with a Nucleotide Integrase Comprising a Wild-type or Modified aI2 Intron RNA and an aI2-Encoded Protein 0.025 O.D.$_{260}$ units of the RNP particles of formulation 1 were reacted with three different derivatives of the DNA wt substrate of FIG. 3. Each of the derivatives contained a single point mutation. In the derivatives the nucleotide at +1 was changed to either a C, G, or A. The derivatives were also reacted with a nucleotide integrase comprising an aI2 intron RNA in which the nucleotide immediately preceding EBS1 was either an A, G, C, or T. The reactions were conducted and the cleavage products assayed on a 1% agarose gel as described in example 1. The results indicated that cleavage of the top strand is enhanced when the nucleotide at +1 is complementary to the nucleotide immediately preceding the EBS1 in the aI2 intron RNA and that cleavage of the sense strand is strongly reduced when the target sequence has a G at the +1 position and the intron RNA has a purine nucleotide (A or G) at the δ position.

EXAMPLE 5

Cleaving Double-Stranded DNA Substrates with a Nucleotide Integrase Comprising an aI1 intron RNA and an aI1 Intron-encoded Protein Double-stranded DNA substrates comprising either the wt sequence or an altered sequence having one of the eleven single point mutations depicted in FIG. 6 were reacted with the RNP particle preparation of Formulation 3. For each reaction, 1.5 nM (150000 cpm) of a double-stranded DNA substrate was mixed with 0.025 OD$_{260}$ units of the RNP particle preparation in 10 μl of 50 mM Tris pH 7.5, 5 mM KCl, 10 mM MgCl$_2$, 5 mM DTT. The reaction mixtures were incubated for 20 minutes at 37° C. The reaction was stopped by adding 70 μl of 28.6 mM EDTA, 0.15 mg/ml tRNA. The nucleic acids were phenol extracted, ethanol precipitated, glyoxylated and analyzed on a 1% agarose gel.

The results indicated that the nucleotide integrase of formulation 3 cleaved substrate DNAs having mutations at positions −23, −20, −17, −16, −15 and −14 as efficiently as a substrate having the wt sequence depicted in FIG. 6. Mutations at positions G(−22), G(−21), A(−19) and A(−18) reduced the efficiency of the cleavage somewhat from 75 to 25% of the cleavage that occurred with the wt sequence. The most critical nucleotide appears to be the C at position(−13). Mutations at this position reduced cleavage of the substrate to less than 1% of that which occurred with the wt sequence.

EXAMPLE 6

Cleaving substrates with a Nucleotide Integrase Comprising an Ll.ltrB Intron RNA and an Ll.ltrB Intron-encoded Protein Double-stranded DNA substrates comprising either the wt sequence or an altered wt sequence having one of the eleven single point mutations depicted in FIG. 8 were reacted with the RNP particle preparation of Formulation 15. The point mutations occur at positions −23 to −13 in the wt sequence. For each reaction, 1.5 nM of a double-stranded DNA substrate was mixed with 0.025 OD$_{260}$ units of the RNP particle preparation in 10 pi of 50 mM Tris pH 7.5, 10 mM KCl, 10 mM MgCl$_2$, 5 mM DTT. The reaction mixtures were incubated for 20 minutes at 37° C. The reaction was stopped by adding 70 μl of 28.6 mM EDTA, 0.15 mg/ml tRNA. The nucleic acids were phenol extracted, ethanol precipitated, glyoxylated and analyzed on a 1% agarose gel The results indicated that the nucleotide integrase of formulation 15 cleaved substrate DNAs having mutations at positions C(−22), C(−18), and A(−14) at levels that were approximately 80% of the levels achieved with a substrate having the wt sequence depicted in FIG. 8. Substrates having point mutations at positions G(−21), A(−20), T(−19) were cleaved at levels that were approximately 40% or less of the levels achieved using substrates having a wt sequence.

EXAMPLE 7

Cleaving a Double-Stranded DNA Substrate with Purified RNP Particles 125 fmoles (150,000 cpm) of an internally-labeled substrate containing of yeast mitochondrial COX1 exons 2 and 3 (E2E3) and comprising the WT sequence shown in FIG. 3 were incubated with 10 μl of each of the fractions obtained from the sucrose gradient in formulation 1a. Taking into account the composition of the fractions, the final reaction medium of 20 μl contained 100 mM KCl, 20 mM MgCl$_2$, 50 mM Tris-HCl, pH 7.5, and 5 mM DTT. Following a 20 minute reaction at 37° C., 30 μl of water, 5 μl 0.3 M NaOAc and 5 μg tRNA were added to the fractions. The reaction products were phenol extracted, ethanol precipitated, glyoxalated, separated on a 1% agarose gel and analyzed by autoradiography of the dried gel. The results indicated that the purified RNP particles of formulation 1a are useful to cleave both strands of a double-stranded DNA substrate and to insert the aI2 intron RNA into the cleavage site.

EXAMPLE 8

Cleaving Both Strands of a Double-stranded DNA Substrate and Attaching a cDNA to the Cleavage Site of the Antisense Strand 0.025 O.D.$_{260}$ units of the RNP particles from formulations 1,2,4,5,6,7,8,9, were incubated with 250 fmoles (300, 000 cpm) of a 142 base pair DNA substrate comprising the WT sequence shown in FIG. 3. DNA incubation products were analyzed in a 6% polyacrylamide/8 M urea gel.

A radiolabeled band corresponding to the 5' fragment was detected when RNP particles of formulations 1 and 2 were incubated with substrates that had been labeled on the 5' end of either the top strand or the bottom strand of the DNA substrate, indicating that these particles cleaved both strands of the DNA substrate. The RNP particles of formulation 1 cleaved the top strand precisely at the exon 2-exon 3 junction. The RNP particles of formulations 1 and 2 cleaved the bottom or antisense strand 10 base pairs downstream from the top or sense strand cleavage site. RNP particles of formulation 1 that had been treated with protease K, or RNase A, or boiled did not cleave either strand.

Radiolabeled bands were also detected when the RNP particles of formulation 4 were incubated with DNA substrates that had been 5' end-labeled on either the sense strand or antisense strand, indicating that this nucleotide integrase cleaved both strands of DNA substrate. The RNP particles of formulation 4 contain a modified, excised aI2 RNA and an aI2-encoded protein which lacks detectable reverse transcriptase activity. Although the extent of cleavage of RNP particles of formulation 4 is somewhat reduced compared to cleavage with the RNP particle preparation of formulation 1, the endonuclease activity of the RNA is present even when the reverse transcriptase activity of the aI2-encoded protein is absent.

The radiolabeled bands were detected when the RNP particles of formulation 5 were incubated with the DNA substrate that had been labeled on the 5' end of either the top or bottom strand. In quantitative assays normalized by either $O.D._{260}$ or soluble aI2 reverse transcriptase activity, the cleavage activities for the top and bottom strands by the RNP particles of formulation 5 were 6% and 25%, respectively, of activities of the RNP particles of formulation 1.

A radiolabeled band corresponding to the 5' fragment was detected when the DNA substrate labeled on the 5' end of the top strand was incubated with the RNP particles of formulation 6, but a band corresponding to the 5' fragment of the top strand was not detected when the RNP particles of formulation 6 were incubated with a DNA substrate that had been labeled on the 5' end of the bottom strand. The RNP particles of formulation 6 contain a modified, excised aI2 intron RNA and an aI2-encoded protein that has an alteration in one of the putative endonuclease motifs. Similar results were obtained with the RNP particles of formulation 7, which contains a modified, excised aI2 intron RNA and an aI2-encoded protein in which the conserved portion of the Zn domain is absent. Likewise, RNP particles of formulations 8 and 9, each of which contains a modified, excised aI2 intron RNA and an aI2-encoded protein in which there is a mutation in the $Zn^{2+}$-like motif, cleaved the sense strand but not the antisense strand of the DNA substrate. For the RNP particles of formulations 6, 7, 8, and 9, the level of sense-strand cleavage was proportional to the amount of RNA-DNA products detected in the agarose gels. These findings indicate that the antisense strand endonuclease activity of the aI2-encoded protein is associated with the Zn domain.

A radiolabeled band corresponding to the 5' fragment was detected when the reconstituted RNP particle preparation of formulation 12 was incubated with substrates that had been labeled on the 5' end of either the sense strand or the antisense strand of the DNA substrate. These results establish that the reconstituted RNP particle preparation cleaves both strands of the DNA substrate.

Thus, both the catalytic RNA molecule of the nucleotide integrase and the intron-encoded protein are required for cleavage of both strands of the double stranded DNA. Certain modifications in the Zn domain and the X domain of intron-encoded protein disrupt the cleavage of the antisense strand of the nucleotide integrase 0.025 $O.D._{260}$ units of the RNP particle preparations of formulations 1, 2, 4 and 5 were combined in 10 µl of reaction medium with 1 µg of plasmid containing the wild-type sequence depicted in FIG. 4. The reaction medium contained 0.2 mM each of dATP, dGTP and dTTP, 10 µCi [a-$^{32}$P]-dCTP (3,000 Ci/mmole; DuPont NEN, Boston, Mass.), 100 mM KCl, and 5 mM dithiothreitol, 2 mM $MgCl_2$, and 50 mM Tris-HCl, pH 8.5. The reaction was initiated by addition of the RNP preparations, incubated for 10 minutes at 37° C., and chased with 0.2 mM dCTP for another 10 minutes. After the chase period, the reactions were terminated by extraction with phenol-CIA (phenol-chloroform-isoamyl alcohol; 25:24:1) in the presence of 0.3 M sodium acetate, pH 7.8, and 5 µg *E. coli* tRNA carrier (Sigma, St. Louis, Mo.). Products were ethanol precipitated twice and resolved in 1% agarose gels containing 90 mM Tris-borate, pH 8.3, 2 mM EDTA and 0.05% ethidium bromide. The results indicated that the RNP particles of formulations 1 and 2 catalyze the formation of a DNA molecule on the cleaved DNA substrate. The results also indicated that a nucleotide integrase which lacks an excised group II intron RNA or which contains a group II intron-encoded protein that lacks a reverse transcriptase domain does not catalyze the formation of a cDNA molecule on the cleaved strand.

Cleavage of single stranded DNA

An aI2 nucleotide integrase comprising an excised aI2 RNA and aI2-encoded protein was used to cleave a single stranded DNA comprising an IBS2 and IBS1 sequence complementary to the EBS1 and EBS2 sequences of the wild-type aI2 intron RNA. The reaction is greatly improved when the 3 nucleotides +1 to +3 can base-pair with the 3 nucleotides immediately upstream of EBS1. The most preferred reaction conditions for cleavage of the substrate and insertion of the intron RNA into the cleavage site by the nucleotide integrase, are 100 mM KCl, 20 mM $MgCl_2$, pH 7.5, 5 mM DTT and 37° C.

What is claimed is:

1. A method of cleaving a double stranded DNA substrate at a cleavage site, said substrate having a recognition site, said method comprising the following steps:
   (a) providing a nucleotide integrase comprising;
      (i) a group II intron RNA having a first hybridization sequence capable of hybridizing with a first intron RNA binding sequence of one strand of the DNA substrate and a second hybridization sequence capable of hybridizing with a second RNA binding sequence on said one strand of the substrate; and
      (ii) a group II intron-encoded protein capable of binding with at least one nucleotide in a first sequence element in the recognition site of the substrate, said group II intron-encoded protein being bound to said group II intron RNA; and
   (b) reacting the nucleotide integrase with the substrate to permit the nucleotide integrase to cleave said one strand of the DNA substrate and to insert the group II intron RNA into the cleavage site.

2. The method of claim 1 wherein there is at least 80% complementarity between the first hybridization sequence and the first intron RNA binding sequence and at least 80% complementarity between the second hybridization sequence and the second intron RNA-binding sequence.

3. The method of claim 1 wherein the group II intron RNA further comprises a δ nucleotide that is complementary to a δ' nucleotide on said one strand of the substrate, said δ' nucleotide being located at position +1 relative to the cleavage site.

4. The method of claim I wherein the group II intron RNA is a wild-type or modified aI2 intron RNA and wherein the group II intron-encoded protein is an aI2 intron-encoded protein.

5. The method of claim 4 wherein said one strand of the substrate comprises a T at position −13 relative to the cleavage site, a T at position −15 relative to the cleavage site, a C at position −18 relative to the cleavage site, and a G at position −16 or position −19 relative to the cleavage site.

6. The method of claim 4 wherein said one strand of said substrate comprises a G at −19, a C at −18, a G at −16, a T at −15, and a T at −13 relative to the cleavage site.

7. The method of claim 1 wherein the group II intron RNA is a wild-type or modified aI1 intron RNA and wherein said group II intron-encoded protein is a protein encoded by an aI1 intron.

8. The method of claim 7 wherein said one strand of the substrate has a C at −13 relative to the cleavage site.

9. The method of claim 7 wherein said one strand of the substrate comprises a G at −22, a G at −21, an A at −19, an A at −18, and a C at −13 relative to the cleavage site.

10. A method of cleaving a double stranded DNA substrate at a cleavage site, said substrate having a recognition site, said method comprising the following steps
   (a) providing a nucleotide integrase comprising;
      (i) a wild-type or modified Ll.ltrB intron RNA, wherein said intron RNA has a first hybridization sequence capable of hybridizing with a first intron RNA binding sequence of one strand of the DNA substrate and a second hybridization sequence capable of hybridizing with a second RNA binding sequence on said one strand of the substrate; and
      (ii) a protein encoded by the Ll.ltrB intron, said protein capable of binding with at least one nucleotide in a first sequence element in the recognition site of the substrate, said protein being bound to said intron RNA; and (b) reacting the nucleotide integrase with the substrate to permit the nucleotide integrase to cleave said one strand of the DNA substrate and to insert the intron RNA into the cleavage site.

11. The method of claim 10 wherein said one strand of the substrate comprises a G at −21 and an A at −20 relative to the cleavage site.

12. The method of claim 11 wherein said one strand of the substrate comprises a G at −21, an A at −20, a T at −19, a G at −17 and a G at −15 relative to the cleavage site.

13. A method of cleaving a single-stranded nucleic acid substrate at a cleavage site comprising the following steps:
(a) providing a nucleotide integrase comprising;
  (i) a group II intron RNA having a first hybridizing sequence capable of hybridizing with a first intron RNA binding sequence on the nucleic acid substrate and a second hybridizing sequence capable of hybridizing with a second intron RNA binding sequence on said nucleic acid substrate, and
  (ii) a group II intron-encoded protein bound to said group II intron RNA; and
(b) reacting the nucleotide integrase with the substrate to permit the nucleotide integrase to cleave the nucleic acid substrate and to insert the group II intron RNA into the cleavage site.

14. The method of claim 13 wherein the substrate is RNA.

15. The method of claim 13 wherein the substrate is DNA.

16. The method of claim 13 wherein the nucleotide integrase is selected from a group consisting of:
(a) a wild-type or modified aI2 intron RNA and an aI2 intron-encoded protein;
(b) a wild-type or modified aI1 intron RNA and an aI1 intron-encoded protein; and
(c) a wild-type or modified Ll.ltrB intron RNA and an Ll.ltrB intron-encoded protein.

17. A method of cleaving both strands of a double-stranded DNA substrate comprising the following steps:
(a) providing a nucleotide integrase comprising;
  (i) a group II intron RNA having a first hybridizing sequence capable of hybridizing with a first intron RNA binding sequence on one strand of the DNA substrate and a second hybridizing sequence capable of hybridizing with a second intron RNA binding sequence on said one strand of the DNA substrate; and
  (ii) a group II intron-encoded protein capable of binding to at least one nucleotide in a first sequence element and to at least one nucleotide in a second sequence element of the substrate, said group II intron-encoded protein being bound to said group II intron RNA; and
(c) reacting the nucleotide integrase with the substrate for a time and at a temperature sufficient to permit the nucleotide integrase to cleave both strands of the DNA substrate and to insert the group II intron RNA into the cleavage site on said one strand.

18. The method of claim 17 wherein the nucleotide integrase is selected from a group consisting of:
(a) a wild-type or modified aI2 intron RNA and an aI2 intron-encoded protein;
(b) a wild-type or modified aI1 intron RNA and an aI1 intron-encoded protein; and
(c) a wild-type or modified Lltr.B intron RNA and an Ll.ltrB intron-encoded protein.

19. The method of claim 17 wherein there is at least 80% complementarity between the first hybridization sequence and the first intron RNA binding sequence and wherein there is at least 80% complementarity between the second hybridization sequence and the second intron RNA binding sequence.

20. The method of claim 17 wherein the group II intron RNA is a wild-type or modified aI2 intron RNA, wherein the group II intron-encoded protein is an aI2 intron-encoded protein; and wherein said one strand of the substrate comprises a C at −18, a T at −15, a T at −13, a G at −13 or −16, a T at +1, a T at +4 and a G at +4.

21. The method of claim 17 wherein the group II intron RNA is a wild-type or modified aI1 intron RNA: wherein the group II intron-encoded protein is a protein encoded by an aI1 intron; and wherein said one strand of the substrate comprises a C at −13, a T at +1, a T at +2, a T at +3, a T at +4, an A at +5, a G at +6, a T at +7, and an A at +8.

22. A method of cleaving both strands of a double-stranded DNA substrate comprising the following steps:
(a) providing a nucleotide integrase comprising;
  (i) a wild-type or modified Ll.ltrB intron RNA, said intron RNA having a first hybridizing sequence capable of hybridizing with a first intron RNA binding sequence on one strand of the DNA substrate and a second hybridizing sequence capable of hybridizing with a second intron RNA binding sequence on said one strand of the DNA substrate; and
  (ii) a protein encoded by an Ll.ltrB intron, said protein capable of binding to at least one nucleotide in a first sequence element and to at least one nucleotide in a second sequence element of the substrate, said protein being bound to said intron RNA; and
(c) reacting the nucleotide integrase with the substrate for a time and at a temperature sufficient to permit the nucleotide integrase to cleave both strands of the DNA substrate and to insert the group II intron RNA into the cleavage site on said one strand.

23. The method of claim 17 wherein the group II intron encoded protein comprises a reverse transcriptase domain, and wherein the nucleotide integrase and the substrate are reacted in a reaction mixture comprising dATP, dGTP, dTTP, and dCTP such that a cDNA molecule is formed in the cleavage site on the other strand of the DNA substrate.

24. A method of detecting the presence of a nucleotide recognition site in a nucleic acid substrate comprising the steps of:
(a) providing a nucleotide integrase capable of cleaving a nucleic acid substrate having a recognition site;
(b) reacting the nucleic acid substrate with said nucleotide integrase; and
(c) assaying for cleavage of the nucleic acid substrate, wherein cleavage is indicative of the presence of the recognition site in the nucleic acid substrate.

25. The method of claim 10 wherein there is at least 80% complementarity between the first hybridization sequence and the first intron RNA binding sequence and at least 80% complementarity between the second hybridization sequence and the second intron RNA-binding sequence.

26. A method of cleaving a single-stranded nucleic acid substrate at a cleavage site comprising the following steps:
(a) providing a nucleotide integrase comprising:
  (i) a wild-type or modified Lltr.B intron RNA, said intron RNA having a first hybridizing sequence capable of hybridizing with a first intron RNA binding sequence on the nucleic acid substrate and a second hybridizing sequence capable of hybridizing with a second intron RNA binding sequence on said nucleic acid substrate, and (ii) an Ll.ltrB intron-encoded protein bound to said intron RNA; and (b) reacting the nucleotide integrase with the substrate to permit the nucleotide integrase to cleave the nucleic acid substrate and to insert the intron RNA into the cleavage site.

27. The method of claim 22 wherein the top strand of the substrate comprises a G at −21, an A at −20, a C at +1, an A at +2, a T at +3, an A at +4, a T at +5, a C at +6, an A at +7, and a T at +8.

* * * * *

UNITED STATES PATENT AND TRADEMARK OFFICE
CERTIFICATE OF CORRECTION

PATENT NO. : 6,027,895
DATED : February 22, 2000
INVENTOR(S) : Alan M. Lambowitz, Steven Zimmerly, Huatao Gau, Georg Mohr and Clifford James Beall It is certified that error appears in the above-indentified patent and that said Letters Patent is hereby corrected as shown below:

On the title page, after "Inventors:" please delete "Allen" and insert --Alan--.

Signed and Sealed this

Third Day of April, 2001

Attest:

NICHOLAS P. GODICI

*Attesting Officer*      *Acting Director of the United States Patent and Trademark Office*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 2483 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO:1:

```
GTGCGCCGTT TCGCTTAATT TATCACTGTA TTGAAGTGTT AATTGATAAA CATATCTCTG      60

TTTATTCAAT TAATGAAAAC TTTACCGTAT CATTTTGGTT CTGATTATTA GTAGTAACAT     120

ACATAGTATT TAGATACGTA AACCATATGG CTTACCCAGT TGGGGCCAAC TCAACGGGGA     180

CAATAGCATG CCATAAAAGC GCTGGAGTAA AACAGCCAGC GCAAGGTAAG AACTGTCCGA    240

TGGCTAGGTT AACGAATTCC TGTAAAGAAT GTTTAGGGTT CTCATTAACT CCTTCCCACT     300

TGGGGATTGT GATTCATGCT TATGTATTGG AAGAAGAGGT ACACGAGTTA ACCAAAAATG    360

AATCATTAGC TTTAAGTAAA AGTTGACATT TGGAGGGCTG TACGAGTTCA AATGGAAAAT    420

TAAGAAATAC GGGATTGTCC GAAAGGGGAA ACCCTGGGGA TAACGGAGTC TTCATAGTAC    480

CCAAATTTAA TTTAAATAAA GCGAGATACT TTAGTACTTT ATCTAAATTA AATGCAAGGA    540

AGGAAGACAG TTTAGCGTAT TTAACAAAGA TTAATACTAC GGATTTTTCC GAGTTAAATA    600

AATTAATAGA AAATAATCAT AATAAACTTG AAACCATTAA TACTAGAATT TTAAAATTAA    660

TGTCAGATAT TAGAATGTTA TTAATTGCTT ATAATAAAAT TAAAAGTAAG AAAGGTAATA    720

TATCTAAAGG TTCTAATAAT ATTACCTTAG ATGGGATTAA TATTTCATAT TTAAATAAAT    780

TATCTAAAGA TATTAACACT AATATGTTTA AATTTTCTCC GGTTAGAAGA GTTGAAATTC    840

CTAAAACATC TGGAGGATTT AGACCTTTAA GTGTTGGAAA TCCTAGAGAA AAAATTGTAC    900

AAGAAAGTAT GAGAATAATA TTAGAAATTA TCTATAATAA TAGTTTCTCT TATTATTCTC    960

ATGGATTTAG ACCTAACTTA TCTTGTTTAA CAGCTATTAT TCAATGTAAA AATTATATGC   1020

AATACTGTAA TTGATTTATT AAAGTAGATT TAAATAAATG CTTTGATACA ATTCCACATA   1080

ATATGTTAAT TAATGTATTA AATGAGAGAA TCAAAGATAA AGGTTTCATA GACTTATTAT   1140

ATAAATTATT AAGAGCTGGA TATGTTGATA AAAATAATAA TTATCATAAT ACAACTTTAG   1200

GAATTCCTCA AGGTAGTGTT GTCAGTCCTA TTTTATGTAA TATTTTTTTA GATAAATTAG   1260

ATAAATATTT AGAAAATAAA TTTGAGAATG AATTCAATAC TGGAAATATG TCTAATAGAG   1320

GTAGAAATCC AATTTATAAT AGTTTATCAT CTAAAATTTA TAGATGTAAA TTATTATCTG   1380

AAAAATTAAA ATTGATTAGA TTAAGAGACC ATTACCAAAG AAATATGGGA TCTGATAAAA   1440

GTTTTAAAAG AGCTTATTTT GTTAGATATG CTGATGATAT TATCATTGGT GTAATGGGTT   1500

CTCATAATGA TTGTAAAAAT ATTTTAAACG ATATTAATAA CTTCTTAAAA GAAAATTTAG   1560

GTATGTCAAT TAATATAGAT AAATCCGTTA TTAAACATTC TAAAGAAGGA GTTAGTTTTT   1620

TAGGGTATGA TGTAAAAGTT ACACCTTGAG AAAAAAGACC TTATAGAATG ATTAAAAAAG   1680

GTGATAATTT TATTAGGGTT AGACATCATA CTAGTTTAGT TGTTAATGCC CCTATTAGAA   1740

GTATTGTAAT AAAATTAAAT AAACATGGCT ATTGTTCTCA TGGTATTTTA GGAAAACCCA   1800

GAGGGGTTGG AAGATTAATT CATGAAGAAA TGAAAACCAT TTAATGCAT TACTTAGCTG    1860

TTGGTAGAGG TATTATAAAC TATTATAGAT TAGCTACCAA TTTTACCACA TTAAGAGGTA   1920

GAATTACATA CATTTTATTT TATTCATGTT GTTAACATT AGCAAGAAAA TTTAAATTAA    1980

ATACTGTTAA GAAAGTTATT TTAAAATTCG GTAAAGTATT AGTTGATCCT CATTCAAAAG   2040

TTAGTTTTAG TATTGATGAT TTTAAAATTA GACATAAAAT AAATATAACT GATTCTAATT   2100

ATACACCTGA TGAAATTTTA GATAGATATA AATATATGTT ACCTAGATCT TTATCATTAT   2160

TTAGTGGTAT TTGTCAAATT TGTGGTTCTA AACATGATTT AGAAGTACAT CACGTAAGAA   2220

CATTAAATAA TGCTGCCAAT AAAATTAAAG ATGATTATTT ATTAGGTAGA ATGATTAAGA   2280

TAAATAGAAA ACAAATTACT ATCTGTAAAA CATGTCATTT TAAAGTTCAT CAAGGTAAAT   2340
```

-continued

| ATAATGGTCC AGGTTTATAA TAATTATTAT ACTATTAAAT ATGCGTTAAA TGGAGAGCCG | 2400 |
| TATGATATGA AAGTATCACG TACGGTTCGG AGAGGGCTCT TTTATATGAA TGTTATTACA | 2460 |
| TTCAGATAGG TTTGCTACTC TAC | 2483 |

(2) INFORMATION FOR SEQ ID NO:2:

(i) SEQUENCE CHARACTERISTICS:
        (A) LENGTH: 2448 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:2:

| GTGCGCCTCT CAGTGCGTAT ATTTCGTTGA TGCGTCTAGC ATTAGTATTA TGAATCATCA | 60 |
| ATAGATACTT AAAACATATG ACTAACTCAG TAGGGGCTAA CTTTACGGGG ACAATAGCAT | 120 |
| GTCATAAAAC ACCTATGATT AGTGTAGGTG GAGTTAAGTG TTACATGGTT AGGTTAACGA | 180 |
| ACTTCTTACA AGTCTTTATC AGGATTACAA TTTCCTCTTA TCATTTGGAT ATAGTAAAAC | 240 |
| AAGTTTGATT ATTTTACGTT GAGGTAATCA GATTATGATT CATTGTTTTA GATAGCACAG | 300 |
| GCAGTGTGAA AAAGATGAAG GACCTAAATA ACACAAAAGG AAATACGAAA AGTGAGGGAT | 360 |
| CAACTGAAAG AGGAAACTCT TGAGTTGACA GAGGTATAGT AGTACCGAAT ACTCAAATAA | 420 |
| AAATGAGATT TTTAAATCAA GTTAGATACT ATTCAGTAAA TAATAATTTA AAAATAGGGA | 480 |
| AGGATACCAA TATTGAGTTA TCAAAAGATA CAAGTACTTC GGACTTGTTA GAATTTGAGA | 540 |
| AATTAGTAAT AGATAATATA AATGAGGAAA ATATAAATAA TAATTTATTA AGTATTATAA | 600 |
| AAAACGTAGA TATATTAATA TTAGCATATA ATAGAATTAA GAGTAAACCT GGTAATATAA | 660 |
| CTCCAGGTAC AACATTAGAA ACATTAGATG GTATAAATAT AATATATTTA AATAAATTAT | 720 |
| CAAATGAATT AGGAACAGGT AAATTCAAAT TTAAACCCAT GAGAATAGTT AATATTCCTA | 780 |
| AACCTAAAGG TGGTATAAGA CCTTTAAGTG TAGGTAATCC AAGAGATAAA ATTGTACAAG | 840 |
| AAGTTATAAG AATAATTTTA GATACAATTT TTGATAAAAA GATATCAACA CATTCACATG | 900 |
| GTTTTAGAAA GAATATAAGT TGTCAAACAG CAATTTGAGA AGTTAGAAAT ATATTTGGTG | 960 |
| GAAGTAATTG ATTTATTGAA GTAGACTTAA AAAAATGTTT TGATACAATT TCTCATGATT | 1020 |
| TAATTATTAA AGAATTAAAA AGATATATTT CAGATAAAGG TTTTATTGAT TTAGTATATA | 1080 |
| AATTATTAAG AGCTGGTTAT ATTGATGAGA AAGGAACTTA TCATAAACCT ATATTAGGTT | 1140 |
| TACCTCAAGG ATCATTAATT AGTCCTATCT TATGTAATAT TGTAATAACA TTGGTAGATA | 1200 |
| ATTGATTAGA AGATTATATT AATTTATATA ATAAAGGTAA AGTTAAAAAA CAACATCCTA | 1260 |
| CATATAAAAA ATTATCAAGA ATAATTGCAA AAGCTAAAAT ATTTTCGACA AGATTAAAAT | 1320 |
| TACATAAAGA AAGAGCTAAA GGCCCACTAT TTATTTATAA TGATCCTAAT TTCAAGAGAA | 1380 |
| TAAAATACGT TAGATATGCA GATGATATTT TAATTGGGGT ATTAGGTTCA AAAAATGATT | 1440 |
| GTAAAATAAT CAAAAGAGAT TTAAACAATT TTTTAAATTC ATTAGGTTTA ACTATAAATG | 1500 |
| AAGAAAAAAC TTTAATTACT TGTGCAACTG AACTACCAGC AAGATTTTTA GGTTATAATA | 1560 |
| TTTCAATTAC ACCTTTAAAA AGAATACCTA CAGTTACTAA ACTAATTAGA GGTAAACTTA | 1620 |
| TTAGAAGTAG AAATACAACT AGACCTATTA TTAATGCACC AATTAGAGAT ATTATCAATA | 1680 |
| AATTAGCTAC TAATGGATAT TGTAAGCATA ATAAAAATGG TAGAATAGGA GTGCCTACAA | 1740 |

-continued

```
GAGTAGGTAG ATGACTATAT GAAGAACCTA GAACAATTAT TAATAATTAT AAAGCGTTAG    1800

GTAGAGGTAT CTTAAATTAT TATAAATTAG CTACTAATTA TAAAAGATTA AGAGAAAGAA    1860

TCTATTACGT ATTATATTAT TCATGTGTAT TAACTTTAGC TAGTAAATAT AGATTAAAAA    1920

CAATAAGTAA AACTATTAAA AAATTTGGTT ATAATTTAAA TATTATTGAA AATGATAAAT    1980

TAATTGCCAA TTTTCCAAGA AATACTTTTG ATAATATCAA AAAAATTGAA AATCATGGTA    2040

TATTTATATA TATATCAGAA GCTAAAGTAA CTGATCCTTT TGAATATATC GATTCAATTA    2100

AATATATATT ACCTACAGCT AAAGCTAATT TTAATAAACC TTGTAGTATT TGTAATTCAA    2160

CTATTGATGT AGAAATACAT CATGTTAAAC AATTACATAG AGGTATATTA AAAGCACTTA    2220

AAGATTATAT TCTAGGTAGA ATAATTACCA TAAACAGAAA ACAAATTCCA TTATGTAAAC    2280

AATGTCATAT TAAAACACAT AAAAATAAAT TTAAAAATAT AGGACCTGGT ATATAAAATC    2340

TATTATTAAT GATACTCAAT ATGGAAAGCC GTATGATGGG AAACTATCAC GTACGGTTTG    2400

GGAAAGGCTC TTTAACACGT GGCAACATAG GTTAATTTGC TATTTCAT              2448
```

(2) INFORMATION FOR SEQ ID NO:3:

(i) SEQUENCE CHARACTERISTICS:
        (A) LENGTH: 777 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:3:

```
Ala Pro Thr Ser Ala Tyr Ile Ser Leu Met Arg Thr Ala Leu Val Leu
1               5                   10                  15

Trp Ile Ile Asn Arg Tyr Leu Lys His Met Thr Asn Ser Val Gly Ala
            20                  25                  30

Asn Phe Thr Gly Thr Met Ala Cys His Lys Thr Pro Met Ile Ser Val
        35                  40                  45

Gly Gly Val Lys Cys Tyr Met Val Arg Leu Thr Asn Phe Leu Gln Val
    50                  55                  60

Phe Ile Arg Ile Thr Ile Ser Ser Tyr His Leu Asp Met Val Lys Gln
65                  70                  75                  80

Val Trp Leu Phe Tyr Val Glu Val Ile Arg Leu Trp Phe Ile Val Leu
                85                  90                  95

Asp Ser Thr Gly Ser Val Lys Lys Met Lys Asp Thr Asn Asn Thr Lys
            100                 105                 110

Gly Asn Thr Lys Ser Glu Gly Ser Thr Glu Arg Gly Asn Ser Trp Val
        115                 120                 125

Asp Arg Gly Met Val Val Pro Asn Thr Gln Met Lys Met Arg Phe Leu
    130                 135                 140

Asn Gln Val Arg Tyr Tyr Ser Val Asn Asn Leu Lys Met Gly Lys
145                 150                 155                 160

Asp Thr Asn Ile Glu Leu Ser Lys Asp Thr Ser Thr Ser Asp Leu Leu
                165                 170                 175

Glu Phe Glu Lys Leu Val Met Asp Asn Met Asn Glu Glu Asn Met Asn
            180                 185                 190

Asn Asn Leu Leu Ser Ile Met Lys Asn Val Asp Met Leu Met Leu Ala
        195                 200                 205

Tyr Asn Arg Ile Lys Ser Lys Pro Gly Asn Met Thr Pro Gly Thr Thr
```

-continued

```
            210                 215                 220
Leu Glu Thr Leu Asp Gly Met Asn Met Met Tyr Leu Asn Lys Leu Ser
225                 230                 235                 240

Asn Glu Leu Gly Thr Gly Lys Phe Lys Phe Lys Pro Met Arg Met Val
                245                 250                 255

Asn Ile Pro Lys Pro Lys Gly Gly Met Arg Pro Leu Ser Val Gly Asn
            260                 265                 270

Pro Arg Asp Lys Ile Val Gln Glu Val Met Arg Met Ile Leu Asp Thr
                275                 280                 285

Ile Phe Asp Lys Lys Met Ser Thr His Ser His Gly Phe Arg Lys Asn
            290                 295                 300

Met Ser Cys Gln Thr Ala Ile Trp Glu Val Arg Asn Met Phe Gly Gly
305                 310                 315                 320

Ser Asn Trp Phe Ile Glu Val Asp Leu Lys Lys Cys Phe Asp Thr Ile
                325                 330                 335

Ser His Asp Leu Ile Ile Lys Glu Leu Lys Arg Tyr Ile Ser Asp Lys
            340                 345                 350

Gly Phe Ile Asp Leu Val Tyr Lys Leu Leu Arg Ala Gly Tyr Ile Asp
                355                 360                 365

Glu Lys Gly Thr Tyr His Lys Pro Met Leu Gly Leu Pro Gln Gly Ser
370                 375                 380

Leu Ile Ser Pro Ile Leu Cys Asn Ile Val Met Thr Leu Val Asp Asn
385                 390                 395                 400

Trp Leu Glu Asp Tyr Ile Asn Leu Tyr Asn Lys Gly Lys Val Lys Lys
                405                 410                 415

Gln His Pro Thr Tyr Lys Lys Leu Ser Arg Met Ile Ala Lys Ala Lys
                420                 425                 430

Met Phe Ser Thr Arg Leu Lys Leu His Lys Glu Arg Ala Lys Gly Pro
            435                 440                 445

Thr Phe Ile Tyr Asn Asp Pro Asn Phe Lys Arg Met Lys Tyr Val Arg
            450                 455                 460

Tyr Ala Asp Asp Ile Leu Ile Gly Val Leu Gly Ser Lys Asn Asp Cys
465                 470                 475                 480

Lys Met Ile Lys Arg Asp Leu Asn Asn Phe Leu Asn Ser Leu Gly Leu
                485                 490                 495

Thr Met Asn Glu Glu Lys Thr Leu Ile Thr Cys Ala Thr Glu Thr Pro
            500                 505                 510

Ala Arg Phe Leu Gly Tyr Asn Ile Ser Ile Thr Pro Leu Lys Arg Met
            515                 520                 525

Pro Thr Val Thr Lys Thr Ile Arg Gly Lys Thr Ile Arg Ser Arg Asn
            530                 535                 540

Thr Thr Arg Pro Ile Ile Asn Ala Pro Ile Arg Asp Ile Ile Asn Lys
545                 550                 555                 560

Leu Ala Thr Asn Gly Tyr Cys Lys His Asn Lys Asn Gly Arg Met Gly
                565                 570                 575

Val Pro Thr Arg Val Gly Arg Trp Thr Tyr Glu Glu Pro Arg Thr Ile
            580                 585                 590

Ile Asn Asn Tyr Lys Ala Leu Gly Arg Gly Ile Leu Asn Tyr Tyr Lys
            595                 600                 605

Leu Ala Thr Asn Tyr Lys Arg Leu Arg Glu Arg Ile Tyr Tyr Val Leu
            610                 615                 620

Tyr Tyr Ser Cys Val Leu Thr Leu Ala Ser Lys Tyr Arg Leu Lys Thr
625                 630                 635                 640
```

```
Met Ser Lys Thr Ile Lys Lys Phe Gly Tyr Asn Leu Asn Ile Ile Glu
                645                 650                 655

Asn Asp Lys Leu Ile Ala Asn Phe Pro Arg Asn Thr Phe Asp Asn Ile
            660                 665                 670

Lys Lys Ile Glu Asn His Gly Met Phe Met Tyr Met Ser Glu Ala Lys
        675                 680                 685

Val Thr Asp Pro Phe Glu Tyr Ile Asp Ser Ile Lys Tyr Met Leu Pro
    690                 695                 700

Thr Ala Lys Ala Asn Phe Asn Lys Pro Cys Ser Ile Cys Asn Ser Thr
705                 710                 715                 720

Ile Asp Val Glu Met His His Val Lys Gln Leu His Arg Gly Met Leu
                725                 730                 735

Lys Ala Thr Lys Asp Tyr Ile Thr Gly Arg Met Ile Thr Met Asn Arg
            740                 745                 750

Lys Gln Ile Pro Leu Cys Lys Gln Cys His Ile Lys Thr His Lys Asn
        755                 760                 765

Lys Phe Lys Asn Met Gly Pro Gly Met
    770                 775
```

(2) INFORMATION FOR SEQ ID NO:4:

(i) SEQUENCE CHARACTERISTICS:
        (A) LENGTH: 785 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:4:

```
Ala Pro Phe Arg Leu Ile Tyr His Cys Ile Glu Val Leu Ile Asp Lys
1               5                   10                  15

His Ile Ser Val Tyr Ser Ile Asn Glu Asn Phe Thr Val Ser Phe Trp
            20                  25                  30

Phe Trp Leu Leu Val Val Thr Tyr Met Val Phe Arg Tyr Val Asn His
        35                  40                  45

Met Ala Tyr Pro Val Gly Ala Asn Ser Thr Gly Thr Met Ala Cys His
    50                  55                  60

Lys Ser Ala Gly Val Lys Gln Pro Ala Gln Gly Lys Asn Cys Pro Met
65                  70                  75                  80

Ala Arg Leu Thr Asn Ser Cys Lys Glu Cys Leu Gly Phe Ser Leu Thr
                85                  90                  95

Pro Ser His Leu Gly Ile Val Ile His Ala Tyr Val Leu Glu Glu Glu
            100                 105                 110

Val His Glu Leu Thr Lys Asn Glu Ser Leu Ala Leu Ser Lys Ser Trp
        115                 120                 125

His Leu Glu Gly Cys Thr Ser Ser Asn Gly Lys Leu Arg Asn Thr Gly
    130                 135                 140

Leu Ser Glu Arg Gly Asn Pro Gly Asp Asn Gly Val Phe Met Val Pro
145                 150                 155                 160

Lys Phe Asn Leu Asn Lys Ala Arg Tyr Phe Ser Thr Leu Ser Lys Leu
                165                 170                 175

Asn Ala Arg Lys Glu Asp Ser Leu Ala Tyr Leu Thr Lys Ile Asn Thr
            180                 185                 190
```

-continued

```
Thr Asp Phe Ser Glu Leu Asn Lys Leu Met Glu Asn His Asn Lys
        195                 200                 205

Thr Glu Thr Ile Asn Thr Arg Ile Leu Lys Leu Met Ser Asp Ile Arg
    210                 215                 220

Met Leu Leu Ile Ala Tyr Asn Lys Ile Lys Ser Lys Lys Gly Asn Met
225                 230                 235                 240

Ser Lys Gly Ser Asn Asn Ile Thr Leu Asp Gly Ile Asn Ile Ser Tyr
                245                 250                 255

Leu Asn Lys Leu Ser Lys Asp Ile Asn Thr Asn Met Phe Lys Phe Ser
            260                 265                 270

Pro Val Arg Arg Val Glu Ile Pro Lys Thr Ser Gly Gly Phe Arg Pro
        275                 280                 285

Leu Ser Val Gly Asn Pro Arg Glu Lys Ile Val Gln Glu Ser Met Arg
    290                 295                 300

Met Met Leu Glu Ile Ile Tyr Asn Asn Ser Phe Ser Tyr Tyr Ser His
305                 310                 315                 320

Gly Phe Arg Pro Asn Leu Ser Cys Leu Thr Ala Ile Ile Gln Cys Lys
                325                 330                 335

Asn Tyr Met Gln Tyr Cys Asn Trp Phe Ile Lys Val Asp Leu Asn Lys
            340                 345                 350

Cys Phe Asp Thr Ile Pro His Asn Met Leu Ile Asn Val Leu Asn Glu
        355                 360                 365

Arg Ile Lys Asp Lys Gly Phe Met Asp Leu Leu Tyr Lys Leu Leu Arg
    370                 375                 380

Ala Gly Tyr Val Asp Lys Asn Asn Tyr His Asn Thr Thr Leu Gly
385                 390                 395                 400

Ile Pro Gln Gly Ser Val Val Ser Pro Ile Leu Cys Asn Ile Phe Leu
                405                 410                 415

Asp Lys Leu Asp Lys Tyr Leu Glu Asn Lys Phe Glu Asn Glu Phe Asn
            420                 425                 430

Thr Gly Asn Met Ser Asn Arg Gly Arg Asn Pro Ile Tyr Asn Ser Leu
        435                 440                 445

Ser Ser Lys Ile Tyr Arg Cys Lys Leu Leu Ser Glu Lys Leu Lys Leu
    450                 455                 460

Ile Arg Leu Arg Asp His Tyr Gln Arg Asn Met Gly Ser Asp Lys Ser
465                 470                 475                 480

Phe Lys Arg Ala Tyr Phe Val Arg Tyr Ala Asp Asp Ile Ile Ile Gly
                485                 490                 495

Val Met Gly Ser His Asn Asp Cys Lys Asn Ile Leu Asn Asp Ile Asn
            500                 505                 510

Asn Phe Leu Lys Glu Asn Leu Ser Ile Val Met Lys Leu Asn Lys His
        515                 520                 525

Gly Tyr Cys Ser His Gly Ile Leu Gly Lys Pro Gly Met Ser Ile Asn
    530                 535                 540

Met Asp Lys Ser Val Ile Lys His Ser Lys Glu Gly Val Ser Phe Leu
545                 550                 555                 560

Gly Tyr Asp Val Lys Val Thr Pro Trp Glu Lys Arg Pro Tyr Arg Met
                565                 570                 575

Ile Lys Lys Gly Asp Asn Phe Ile Arg Val Arg His Thr Ser Leu
            580                 585                 590

Val Val Asn Ala Pro Ile Arg Arg Gly Val Gly Arg Leu Ile His Glu
        595                 600                 605

Glu Met Lys Thr Ile Leu Met His Tyr Leu Ala Val Gly Arg Gly Ile
```

```
              610                 615                 620
Met Asn Tyr Tyr Arg Leu Ala Thr Asn Phe Thr Thr Leu Arg Gly Arg
625                 630                 635                 640

Ile Thr Tyr Ile Leu Phe Tyr Ser Cys Cys Leu Thr Leu Ala Arg Lys
                645                 650                 655

Phe Lys Leu Asn Thr Val Lys Lys Val Ile Leu Lys Phe Gly Lys Val
                660                 665                 670

Leu Val Asp Pro His Ser Lys Val Ser Phe Ser Ile Asp Asp Phe Lys
                675                 680                 685

Ile Arg His Lys Met Asn Met Thr Asp Ser Asn Tyr Thr Pro Asp Glu
690                 695                 700

Ile Leu Asp Arg Tyr Lys Tyr Met Leu Pro Arg Ser Leu Ser Leu Phe
705                 710                 715                 720

Ser Gly Ile Cys Gln Ile Cys Gly Ser Lys His Asp Leu Glu Val His
                725                 730                 735

His Val Arg Thr Leu Asn Asn Ala Ala Asn Lys Ile Lys Asp Asp Tyr
                740                 745                 750

Leu Leu Gly Arg Met Ile Lys Met Asn Arg Lys Gln Ile Thr Ile Cys
                755                 760                 765

Lys Thr Cys His Phe Lys Val His Gln Gly Lys Tyr Asn Gly Pro Gly
                770                 775                 780

Leu
785

(2) INFORMATION FOR SEQ ID NO:5:

(i) SEQUENCE CHARACTERISTICS:
        (A) LENGTH: 2761 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

AAGCTTAGAG AAAAATAATG CGGTGCTTGG TCATCACCTC ATCCAATCAT TTTCTCCTGA      60

TGACAATCTA ACTCCTGAAC AAATTCATGA AATAGGTCGT CAAACCATAT TAGAATTTAC    120

AGGTGGCGAA TATGAATTTG TGATTGCAAC CCACGTCGAT CGTGAACACA TCCATAACGT    180

GCGCCCAGAT AGGGTGTTAA GTCAAGTAGT TTAAGGTACT ACTCTGTAAG ATAACACAGA    240

AAACAGCCAA CCTAACCGAA AAGCGAAAGC TGATACGGGA ACAGAGCACG GTTGGAAAGC    300

GATGAGTTAC CTAAAGACAA TCGGGTACGA CTGAGTCGCA ATGTTAATCA GATATAAGGT    360

ATAAGTTGTG TTTACTGAAC GCAAGTTTCT AATTTCGGTT ATGTGTCGAT AGAGGAAAGT    420

GTCTGAAACC TCTAGTACAA AGAAAGGTAA GTTATGGTTG TGGACTTATC TGTTATCACC    480

ACATTTGTAC AATCTGTAGG AGAACCTATG GGAACGAAAC GAAAGCGATG CCGAGAATCT    540

GAATTTACCA AGACTTAACA CTAACTGGGG ATACCCTAAA CAAGAATGCC TAATAGAAAG    600

GAGGAAAAAG GCTATAGCAC TAGAGCTTGA AAATCTTGCA AGGGTACGGA GTACTCGTAG    660

TATTCTGAGA AGGGTAACGC CCTTTACATG GCAAAGGGGT ACAGTTATTG TGTACTAAAA    720

TTAAAAATTG ATTAGGGAGG AAAACCTCAA AATGAAACCA ACAATGGCAA TTTTAGAAAG    780

AATCAGTAAA AATTCACAAG AAAATATAGA CGAAGTTTTT ACAAGACTTT ATCGTTATCT    840

TTTACGTCCA GATATTTATT ACGTGGCGTA TCAAAATTTA TATTCCAATA AAGGAGCTTC    900

CACAAAAGGA ATATTAGATG ATACAGCGGA TGGCTTTAGT GAAGAAAAAA TAAAAAAGAT    960
```

```
TATTCAATCT TTAAAAGACG GAACTTACTA TCCTCAACCT GTACGAAGAA TGTATATTGC    1020

AAAAAAGAAT TCTAAAAAGA TGAGACCTTT AGGAATTCCA ACTTTCACAG ATAAATTGAT    1080

CCAAGAAGCT GTGAGAATAA TTCTTGAATC TATCTATGAA CCGGTATTCG AAGATGTGTC    1140

TCACGGTTTT AGACCTCAAC GAAGCTGTCA CACAGCTTTG AAAACAATCA AAAGAGAGTT    1200

TGGCGGCGCA AGATGGTTTG TGGAGGGAGA TATAAAAGGC TGCTTCGATA ATATAGACCA    1260

CGTTACACTC ATTGGACTCA TCAATCTTAA AATCAAAGAT ATGAAAATGA GCCAATTGAT    1320

TTATAAATTT CTAAAAGCAG GTTATCTGGA AAACTGGCAG TATCACAAAA CTTACAGCGG    1380

AACACCTCAA GGTGGAATTC TATCTCCTCT TTTGGCCAAC ATCTATCTTC ATGAATTGGA    1440

TAAGTTTGTT TTACAACTCA AAATGAAGTT TGACCGAGAA AGTCCAGAAA GAATAACACC    1500

TGAATATCGG GAACTTCACA ATGAGATAAA AAGAATTTCT CACCGTCTCA AGAAGTTGGA    1560

GGGTGAAGAA AAAGCTAAAG TTCTTTTAGA ATATCAAGAA AAACGTAAAA GATTACCCAC    1620

ACTCCCCTGT ACCTCACAGA CAAATAAAGT ATTGAAATAC GTCCGGTATG CGGACGACTT    1680

CATTATCTCT GTTAAAGGAA GCAAAGAGGA CTGTCAATGG ATAAAAGAAC AATTAAAACT    1740

TTTTATTCAT AACAAGCTAA AAATGGAATT GAGTGAAGAA AAAACACTCA TCACACATAG    1800

CAGTCAACCC GCTCGTTTTC TGGGATATGA TATACGAGTA AGGAGAAGTG GAACGATAAA    1860

ACGATCTGGT AAAGTCAAAA AGAGAACACT CAATGGGAGT GTAGAACTCC TTATTCCTCT    1920

TCAAGACAAA ATTCGTCAAT TTATTTTTGA CAAGAAAATA GCTATCCAAA AGAAAGATAG    1980

CTCATGGTTT CCAGTTCACA GGAAATATCT TATTCGTTCA ACAGACTTAG AAATCATCAC    2040

AATTTATAAT TCTGAATTAA GAGGGATTTG TAATTACTAC GGTCTAGCAA GTAATTTTAA    2100

CCAGCTCAAT TATTTTGCTT ATCTTATGGA ATACAGCTGT CTAAAAACGA TAGCCTCCAA    2160

ACATAAGGGA ACACTTTCAA AAACCATTTC CATGTTTAAA GATGGAAGTG GTTCGTGGGG    2220

CATCCCGTAT GAGATAAAGC AAGGTAAGCA GCGCCGTTAT TTTGCAAATT TTAGTGAATG    2280

TAAATCCCCT TATCAATTTA CGGATGAGAT AAGTCAAGCT CCTGTATTGT ATGGCTATGC    2340

CCGGAATACT CTTGAAAACA GGTTAAAAGC TAAATGTTGT GAATTATGTG AACATCTGA    2400

TGAAAATACT TCCTATGAAA TTCACCATGT CAATAAGGTC AAAAATCTTA AAGGCAAAGA    2460

AAAATGGGAA ATGGCAATGA TAGCGAAACA ACGTAAAACT CTTGTTGTAT GCTTTCATTG    2520

TCATCGTCAC GTGATTCATA ACACAAGTG AATTTTTACG AACGAACAAT AACAGAGCCG    2580

TATACTCCGA GAGGGGTACG TACGGTTCCC GAAGAGGGTG GTGCAAACCA GTCACAGTAA    2640

TGTGAACAAG GCGGTACCTC CCTACTTCAC CATATCATTT TTAATTCTAC GAATCTTTAT    2700

ACTGGCAAAC AATTTGACTG GAAAGTCATT CCTAAAGAGA AAACAAAAAG CGGCAAAGCT    2760

T                                                                  2761
```

(2) INFORMATION FOR SEQ ID NO:6:

(i) SEQUENCE CHARACTERISTICS:
        (A) LENGTH: 1800 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1800

(xi) SEQUENCE DESCRIPTION: SEQ ID NO:6:

-continued

```
ATG AAA CCA ACA ATG GCA ATT TTA GAA AGA ATC AGT AAA AAT TCA CAA      48
Met Lys Pro Thr Met Ala Ile Leu Glu Arg Ile Ser Lys Asn Ser Gln
 1               5                  10                  15

GAA AAT ATA GAC GAA GTT TTT ACA AGA CTT TAT CGT TAT CTT TTA CGT      96
Glu Asn Ile Asp Glu Val Phe Thr Arg Leu Tyr Arg Tyr Leu Leu Arg
             20                  25                  30

CCA GAT ATT TAT TAC GTG GCG TAT CAA AAT TTA TAT TCC AAT AAA GGA     144
Pro Asp Ile Tyr Tyr Val Ala Tyr Gln Asn Leu Tyr Ser Asn Lys Gly
                 35                  40                  45

GCT TCC ACA AAA GGA ATA TTA GAT GAT ACA GCG GAT GGC TTT AGT GAA     192
Ala Ser Thr Lys Gly Ile Leu Asp Asp Thr Ala Asp Gly Phe Ser Glu
         50                  55                  60

GAA AAA ATA AAA AAG ATT ATT CAA TCT TTA AAA GAC GGA ACT TAC TAT     240
Glu Lys Ile Lys Lys Ile Ile Gln Ser Leu Lys Asp Gly Thr Tyr Tyr
 65                  70                  75                  80

CCT CAA CCT GTA CGA AGA ATG TAT ATT GCA AAA AAG AAT TCT AAA AAG     288
Pro Gln Pro Val Arg Arg Met Tyr Ile Ala Lys Lys Asn Ser Lys Lys
                 85                  90                  95

ATG AGA CCT TTA GGA ATT CCA ACT TTC ACA GAT AAA TTG ATC CAA GAA     336
Met Arg Pro Leu Gly Ile Pro Thr Phe Thr Asp Lys Leu Ile Gln Glu
            100                 105                 110

GCT GTG AGA ATA ATT CTT GAA TCT ATC TAT GAA CCG GTA TTC GAA GAT     384
Ala Val Arg Ile Ile Leu Glu Ser Ile Tyr Glu Pro Val Phe Glu Asp
            115                 120                 125

GTG TCT CAC GGT TTT AGA CCT CAA CGA AGC TGT CAC ACA GCT TTG AAA     432
Val Ser His Gly Phe Arg Pro Gln Arg Ser Cys His Thr Ala Leu Lys
        130                 135                 140

ACA ATC AAA AGA GAG TTT GGC GGC GCA AGA TGG TTT GTG GAG GGA GAT     480
Thr Ile Lys Arg Glu Phe Gly Gly Ala Arg Trp Phe Val Glu Gly Asp
145                 150                 155                 160

ATA AAA GGC TGC TTC GAT AAT ATA GAC CAC GTT ACA CTC ATT GGA CTC     528
Ile Lys Gly Cys Phe Asp Asn Ile Asp His Val Thr Leu Ile Gly Leu
                165                 170                 175

ATC AAT CTT AAA ATC AAA GAT ATG AAA ATG AGC CAA TTG ATT TAT AAA     576
Ile Asn Leu Lys Ile Lys Asp Met Lys Met Ser Gln Leu Ile Tyr Lys
            180                 185                 190

TTT CTA AAA GCA GGT TAT CTG GAA AAC TGG CAG TAT CAC AAA ACT TAC     624
Phe Leu Lys Ala Gly Tyr Leu Glu Asn Trp Gln Tyr His Lys Thr Tyr
            195                 200                 205

AGC GGA ACA CCT CAA GGT GGA ATT CTA TCT CCT CTT TTG GCC AAC ATC     672
Ser Gly Thr Pro Gln Gly Gly Ile Leu Ser Pro Leu Leu Ala Asn Ile
        210                 215                 220

TAT CTT CAT GAA TTG GAT AAG TTT GTT TTA CAA CTC AAA ATG AAG TTT     720
Tyr Leu His Glu Leu Asp Lys Phe Val Leu Gln Leu Lys Met Lys Phe
225                 230                 235                 240

GAC CGA GAA AGT CCA GAA AGA ATA ACA CCT GAA TAT CGG GAA CTT CAC     768
Asp Arg Glu Ser Pro Glu Arg Ile Thr Pro Glu Tyr Arg Glu Leu His
                245                 250                 255

AAT GAG ATA AAA AGA ATT TCT CAC CGT CTC AAG AAG TTG GAG GGT GAA     816
Asn Glu Ile Lys Arg Ile Ser His Arg Leu Lys Lys Leu Glu Gly Glu
            260                 265                 270

GAA AAA GCT AAA GTT CTT TTA GAA TAT CAA GAA AAA CGT AAA AGA TTA     864
Glu Lys Ala Lys Val Leu Leu Glu Tyr Gln Glu Lys Arg Lys Arg Leu
            275                 280                 285

CCC ACA CTC CCC TGT ACC TCA CAG ACA AAT AAA GTA TTG AAA TAC GTC     912
Pro Thr Leu Pro Cys Thr Ser Gln Thr Asn Lys Val Leu Lys Tyr Val
        290                 295                 300

CGG TAT GCG GAC GAC TTC ATT ATC TCT GTT AAA GGA AGC AAA GAG GAC     960
Arg Tyr Ala Asp Asp Phe Ile Ile Ser Val Lys Gly Ser Lys Glu Asp
```

```
305                      310                      315                      320
TGT CAA TGG ATA AAA GAA CAA TTA AAA CTT TTT ATT CAT AAC AAG CTA         1008
Cys Gln Trp Ile Lys Glu Gln Leu Lys Leu Phe Ile His Asn Lys Leu
                325                      330                      335

AAA ATG GAA TTG AGT GAA GAA AAA ACA CTC ATC ACA CAT AGC AGT CAA         1056
Lys Met Glu Leu Ser Glu Glu Lys Thr Leu Ile Thr His Ser Ser Gln
                340                      345                      350

CCC GCT CGT TTT CTG GGA TAT GAT ATA CGA GTA AGG AGA AGT GGA ACG         1104
Pro Ala Arg Phe Leu Gly Tyr Asp Ile Arg Val Arg Arg Ser Gly Thr
                355                      360                      365

ATA AAA CGA TCT GGT AAA GTC AAA AAG AGA ACA CTC AAT GGG AGT GTA         1152
Ile Lys Arg Ser Gly Lys Val Lys Lys Arg Thr Leu Asn Gly Ser Val
    370                      375                      380

GAA CTC CTT ATT CCT CTT CAA GAC AAA ATT CGT CAA TTT ATT TTT GAC         1200
Glu Leu Leu Ile Pro Leu Gln Asp Lys Ile Arg Gln Phe Ile Phe Asp
385                      390                      395                      400

AAG AAA ATA GCT ATC CAA AAG AAA GAT AGC TCA TGG TTT CCA GTT CAC         1248
Lys Lys Ile Ala Ile Gln Lys Lys Asp Ser Ser Trp Phe Pro Val His
                    405                      410                      415

AGG AAA TAT CTT ATT CGT TCA ACA GAC TTA GAA ATC ATC ACA ATT TAT         1296
Arg Lys Tyr Leu Ile Arg Ser Thr Asp Leu Glu Ile Ile Thr Ile Tyr
                420                      425                      430

AAT TCT GAA TTA AGA GGG ATT TGT AAT TAC TAC GGT CTA GCA AGT AAT         1344
Asn Ser Glu Leu Arg Gly Ile Cys Asn Tyr Tyr Gly Leu Ala Ser Asn
                435                      440                      445

TTT AAC CAG CTC AAT TAT TTT GCT TAT CTT ATG GAA TAC AGC TGT CTA         1392
Phe Asn Gln Leu Asn Tyr Phe Ala Tyr Leu Met Glu Tyr Ser Cys Leu
    450                      455                      460

AAA ACG ATA GCC TCC AAA CAT AAG GGA ACA CTT TCA AAA ACC ATT TCC         1440
Lys Thr Ile Ala Ser Lys His Lys Gly Thr Leu Ser Lys Thr Ile Ser
465                      470                      475                      480

ATG TTT AAA GAT GGA AGT GGT TCG TGG GGC ATC CCG TAT GAG ATA AAG         1488
Met Phe Lys Asp Gly Ser Gly Ser Trp Gly Ile Pro Tyr Glu Ile Lys
                    485                      490                      495

CAA GGT AAG CAG CGC CGT TAT TTT GCA AAT TTT AGT GAA TGT AAA TCC         1536
Gln Gly Lys Gln Arg Arg Tyr Phe Ala Asn Phe Ser Glu Cys Lys Ser
                500                      505                      510

CCT TAT CAA TTT ACG GAT GAG ATA AGT CAA GCT CCT GTA TTG TAT GGC         1584
Pro Tyr Gln Phe Thr Asp Glu Ile Ser Gln Ala Pro Val Leu Tyr Gly
                515                      520                      525

TAT GCC CGG AAT ACT CTT GAA AAC AGG TTA AAA GCT AAA TGT TGT GAA         1632
Tyr Ala Arg Asn Thr Leu Glu Asn Arg Leu Lys Ala Lys Cys Cys Glu
    530                      535                      540

TTA TGT GGA ACA TCT GAT GAA AAT ACT TCC TAT GAA ATT CAC CAT GTC         1680
Leu Cys Gly Thr Ser Asp Glu Asn Thr Ser Tyr Glu Ile His His Val
545                      550                      555                      560

AAT AAG GTC AAA AAT CTT AAA GGC AAA GAA AAA TGG GAA ATG GCA ATG         1728
Asn Lys Val Lys Asn Leu Lys Gly Lys Glu Lys Trp Glu Met Ala Met
                    565                      570                      575

ATA GCG AAA CAA CGT AAA ACT CTT GTT GTA TGC TTT CAT TGT CAT CGT         1776
Ile Ala Lys Gln Arg Lys Thr Leu Val Val Cys Phe His Cys His Arg
                580                      585                      590

CAC GTG ATT CAT AAA CAC AAG TGA                                         1800
His Val Ile His Lys His Lys  *
                595                      600
```

(2) INFORMATION FOR SEQ ID NO:7:

(i) SEQUENCE CHARACTERISTICS:
        (A) LENGTH: 599 amino acids (B) TYPE: amino acid
(D) TOPOLOGY: linear (ii) MOLECULE TYPE: protein (xi) SEQUENCE DESCRIPTION: SEQ ID NO:7:

```
Met Lys Pro Thr Met Ala Ile Leu Glu Arg Ile Ser Lys Asn Ser Gln
 1               5                  10                  15

Glu Asn Ile Asp Glu Val Phe Thr Arg Leu Tyr Arg Tyr Leu Leu Arg
            20                  25                  30

Pro Asp Ile Tyr Tyr Val Ala Tyr Gln Asn Leu Tyr Ser Asn Lys Gly
        35                  40                  45

Ala Ser Thr Lys Gly Ile Leu Asp Asp Thr Ala Asp Gly Phe Ser Glu
    50                  55                  60

Glu Lys Ile Lys Lys Ile Ile Gln Ser Leu Lys Asp Gly Thr Tyr Tyr
 65                  70                  75                  80

Pro Gln Pro Val Arg Arg Met Tyr Ile Ala Lys Lys Asn Ser Lys Lys
                85                  90                  95

Met Arg Pro Leu Gly Ile Pro Thr Phe Thr Asp Lys Leu Ile Gln Glu
            100                 105                 110

Ala Val Arg Ile Ile Leu Glu Ser Ile Tyr Glu Pro Val Phe Glu Asp
        115                 120                 125

Val Ser His Gly Phe Arg Pro Gln Arg Ser Cys His Thr Ala Leu Lys
    130                 135                 140

Thr Ile Lys Arg Glu Phe Gly Gly Ala Arg Trp Phe Val Glu Gly Asp
145                 150                 155                 160

Ile Lys Gly Cys Phe Asp Asn Ile Asp His Val Thr Leu Ile Gly Leu
                165                 170                 175

Ile Asn Leu Lys Ile Lys Asp Met Lys Met Ser Gln Leu Ile Tyr Lys
            180                 185                 190

Phe Leu Lys Ala Gly Tyr Leu Glu Asn Trp Gln Tyr His Lys Thr Tyr
        195                 200                 205

Ser Gly Thr Pro Gln Gly Gly Ile Leu Ser Pro Leu Leu Ala Asn Ile
    210                 215                 220

Tyr Leu His Glu Leu Asp Lys Phe Val Leu Gln Leu Lys Met Lys Phe
225                 230                 235                 240

Asp Arg Glu Ser Pro Glu Arg Ile Thr Pro Glu Tyr Arg Glu Leu His
                245                 250                 255

Asn Glu Ile Lys Arg Ile Ser His Arg Leu Lys Lys Leu Glu Gly Glu
            260                 265                 270

Glu Lys Ala Lys Val Leu Leu Glu Tyr Gln Glu Lys Arg Lys Arg Leu
        275                 280                 285

Pro Thr Leu Pro Cys Thr Ser Gln Thr Asn Lys Val Leu Lys Tyr Val
    290                 295                 300

Arg Tyr Ala Asp Asp Phe Ile Ile Ser Val Lys Gly Ser Lys Glu Asp
305                 310                 315                 320

Cys Gln Trp Ile Lys Glu Gln Leu Lys Leu Phe Ile His Asn Lys Leu
                325                 330                 335

Lys Met Glu Leu Ser Glu Glu Lys Thr Leu Ile Thr His Ser Ser Gln
            340                 345                 350

Pro Ala Arg Phe Leu Gly Tyr Asp Ile Arg Val Arg Arg Ser Gly Thr
        355                 360                 365

Ile Lys Arg Ser Gly Lys Val Lys Arg Thr Leu Asn Gly Ser Val
    370                 375                 380
```

-continued

```
Glu Leu Leu Ile Pro Leu Gln Asp Lys Ile Arg Gln Phe Ile Phe Asp
385                 390                 395                 400

Lys Lys Ile Ala Ile Gln Lys Lys Asp Ser Ser Trp Phe Pro Val His
                405                 410                 415

Arg Lys Tyr Leu Ile Arg Ser Thr Asp Leu Glu Ile Ile Thr Ile Tyr
                420                 425                 430

Asn Ser Glu Leu Arg Gly Ile Cys Asn Tyr Tyr Gly Leu Ala Ser Asn
            435                 440                 445

Phe Asn Gln Leu Asn Tyr Phe Ala Tyr Leu Met Glu Tyr Ser Cys Leu
        450                 455                 460

Lys Thr Ile Ala Ser Lys His Lys Gly Thr Leu Ser Lys Thr Ile Ser
465                 470                 475                 480

Met Phe Lys Asp Gly Ser Gly Ser Trp Gly Ile Pro Tyr Glu Ile Lys
                485                 490                 495

Gln Gly Lys Gln Arg Arg Tyr Phe Ala Asn Phe Ser Glu Cys Lys Ser
                500                 505                 510

Pro Tyr Gln Phe Thr Asp Glu Ile Ser Gln Ala Pro Val Leu Tyr Gly
            515                 520                 525

Tyr Ala Arg Asn Thr Leu Glu Asn Arg Leu Lys Ala Lys Cys Cys Glu
        530                 535                 540

Leu Cys Gly Thr Ser Asp Glu Asn Thr Ser Tyr Glu Ile His His Val
545                 550                 555                 560

Asn Lys Val Lys Asn Leu Lys Gly Lys Glu Lys Trp Glu Met Ala Met
                565                 570                 575

Ile Ala Lys Gln Arg Lys Thr Leu Val Val Cys Phe His Cys His Arg
                580                 585                 590

His Val Ile His Lys His Lys
                595

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

CATCACGTAA GA                                              12

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GCAGCTGCAG CT                                              12

(2) INFORMATION FOR SEQ ID NO:10:

(i) SEQUENCE CHARACTERISTICS:
```

```
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:10:

CATCATCATC ATCATCAT                                                      18

(2) INFORMATION FOR SEQ ID NO:11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

GTCATGCTGT ATTAATGA                                                      18

(2) INFORMATION FOR SEQ ID NO:12:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

ATGGTAATTC ACAATTAT                                                      18
```